(12) United States Patent
Steiner et al.

(10) Patent No.: US 11,879,778 B2
(45) Date of Patent: Jan. 23, 2024

(54) METHOD FOR CLASSIFYING SPECTRA OF OBJECTS HAVING COMPLEX INFORMATION CONTENT

(71) Applicant: TECHNISCHE UNIVERSITÄAT DRESDEN, Dresden (DE)

(72) Inventors: Gerald Steiner, Schwarzenberg (DE); Grit Preusse, Radebeul (DE); Edmund Koch, Dresden (DE); Roberta Galli, Dresden (DE); Christian Schnabel, Dresden (DE); Johanna Preusse, Radebeul (DE)

(73) Assignee: TECHNISCHE UNIVERSITÄT DRESDEN, Dresden Sachsen (DE)

( * ) Notice: Subject to any disclaimer, the term of this patent is extended or adjusted under 35 U.S.C. 154(b) by 1313 days.

(21) Appl. No.: 16/333,734

(22) PCT Filed: Sep. 15, 2017

(86) PCT No.: PCT/EP2017/073236
§ 371 (c)(1),
(2) Date: Jun. 18, 2019

(87) PCT Pub. No.: WO2018/050802
PCT Pub. Date: Mar. 22, 2018

(65) Prior Publication Data
US 2021/0248429 A1  Aug. 12, 2021

(30) Foreign Application Priority Data
Sep. 16, 2016  (DE) ..................... 10 2016 011 348.0

(51) Int. Cl.
*G01J 3/28* (2006.01)
*G06N 3/08* (2023.01)
(Continued)

(52) U.S. Cl.
CPC .............. *G01J 3/28* (2013.01); *A61B 5/0075* (2013.01); *G01N 33/08* (2013.01);
(Continued)

(58) Field of Classification Search
CPC .. G06K 9/628; G06K 9/00536; A61B 5/0075; G01N 33/08; G01N 21/65;
(Continued)

(56) References Cited

U.S. PATENT DOCUMENTS 6,029,080 A    2/2000  Reynnells et al.
8,880,354 B2   11/2014 Wilkes et al.
(Continued)

FOREIGN PATENT DOCUMENTS

DE   10 2007 013 107   9/2008
DE   10 2008 040838    2/2009
(Continued)

OTHER PUBLICATIONS

Zhihui et al, "Abnormal eggs detection based on spectroscopy technology and multiple classifier fusion" (published in Transactions of the Chinese Society of Agricultural Engineering, vol. 31, Issue 2, pp. 312-318, Jan. 2015) (Year: 2015).*
(Continued)

*Primary Examiner* — Casey L Kretzer
(74) *Attorney, Agent, or Firm* — GREENBLUM & BERNSTEIN, P.L.C.

(57) ABSTRACT

The invention relates to a method for classifying spectra of objects having complex information content after recording of the spectra involving the use of a method for preprocessing data and of a method, associated with the data preprocessing, for classification with the calculation of a classifier. After the recording of the spectra and the preprocessing of the spectra, a multiple classification method is thereby performed with at least two different methods for the data (Continued)

preprocessing of the spectra and the method, assigned to the respective data preprocessing, for classification. After the recording and the data preprocessing of the spectra, the following steps are thereby carried out: a calculation of multiple classifiers of the series per type of data preprocessing; a determination of the classifiers of the series with iterative adjustment and validation; a calculation of probabilities of the class association, with all classifiers of the series or classifiers being equally incorporated into the determination of a classification result.

18 Claims, 13 Drawing Sheets

(51) Int. Cl.
  *G01N 33/08* (2006.01)
  *A61B 5/00* (2006.01)
  *G06F 18/2431* (2023.01)
  *G01N 21/65* (2006.01)

(52) U.S. Cl.
  CPC ........... *G06F 18/2431* (2023.01); *G06N 3/08* (2013.01); *G01N 21/65* (2013.01); *G06F 2218/12* (2023.01)

(58) Field of Classification Search
  CPC .......... G06N 3/08; G01J 3/28; G06F 18/2431; G06F 2218/12
  See application file for complete search history.

(56) References Cited

U.S. PATENT DOCUMENTS

| | | | |
|---|---|---|---|
| 2005/0149300 A1* | 7/2005 | Ruchti | G01N 21/359 703/2 |
| 2005/0286772 A1 | 12/2005 | Albertelli | |
| 2008/0005081 A1* | 1/2008 | Green | G06F 16/48 |
| 2008/0025591 A1 | 1/2008 | Bhanot et al. | |
| 2012/0016818 A1* | 1/2012 | Hackett | G06V 20/69 706/12 |
| 2012/0321174 A1 | 12/2012 | Tsymbal et al. | |
| 2016/0239953 A1* | 8/2016 | Ngadi | G06T 7/0012 |
| 2017/0140299 A1* | 5/2017 | Tanji | G06N 20/00 |

FOREIGN PATENT DOCUMENTS

| | | |
|---|---|---|
| DE | 10 2010 006 161 | 1/2011 |
| DE | 10 2014 010 150 | 1/2016 |
| EP | 2 336 751 | 6/2011 |
| WO | 2010/150 265 | 12/2010 |
| WO | 2014/021 715 | 2/2014 |
| WO | 2016/000 678 | 1/2016 |
| WO | WO-2016006203 A1 * | 1/2016 ........... G01N 21/274 |

OTHER PUBLICATIONS

A.E. Nikulin et al., "Near-optimal region selection for feature space reduction: novel preprocessing methods for classifying MR spectra", NMR Biomed, 11 (4-5), 1998, pp. 719-727.
B.K. Lavine et al., "Genetic algorithms for spectral pattern recognition", Vibrational Spectroscopy, vol. 28, Issue 1, 2002, pp. 83-95.
J. Jacques et al., "Gaussian mixture models for the classification of high-dimensional vibrational spectroscopy data", Journal of Chemometrics, vol. 24, Issue 11-12, 2010, pp. 719-727.
G. Steiner et al., "Rapid and Label-Free Classification of Human Glioma Cells by Infrared Spectroscopic Imaging", Cytometry Part A 2008, 73A, 2008, pp. 1158-1164.
Official Communication issued in International Bureau of WIPO Patent Application No. PCT/EP2017/073236, dated Apr. 1, 2018, along with an English translation thereof.
Official Communication issued in World Intellectual Property Organization Patent Application No. PCT/EP2017/073236, dated Jan. 4, 2018, along with an English translation thereof.
German Office Action conducted in counterpart German Patent Appl. No. DE 10 2016 011 348.0, dated Jun. 7, 2017.
German Office Action conducted in counterpart German Patent Appl. No. DE 10 2016 011 348.0, dated Oct. 22, 2018.
Swierenga et al., "Strategy for constructing robust multivariate calibration models," Chemometrics and Intelligent Laboratory Systems, 1, (Jun. 9, 1999) pp. 1-17; ISSN 0169-7439; https://doi.org/10.1016/S0169-7439(99)0028-3 (Abstract).

* cited by examiner

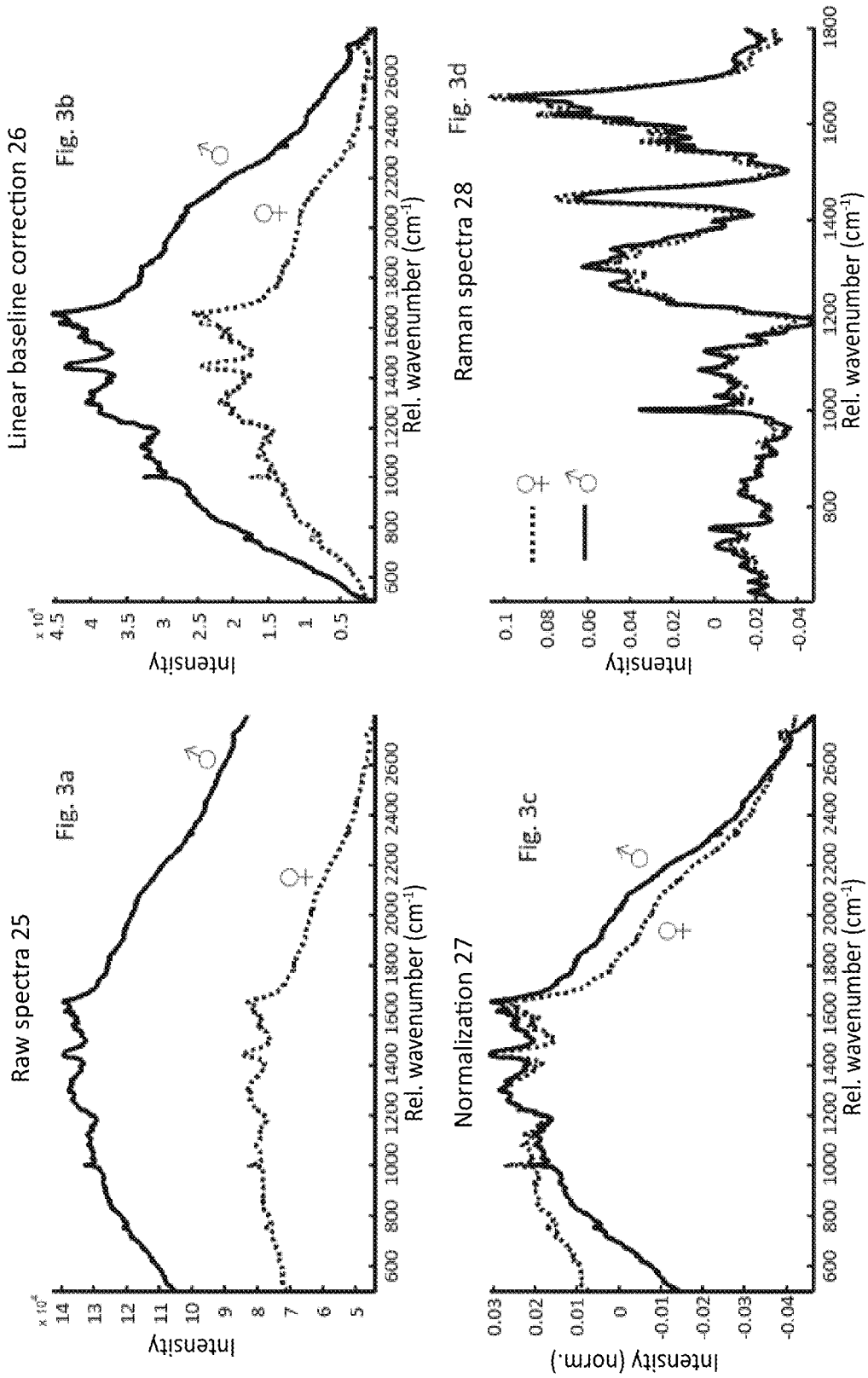

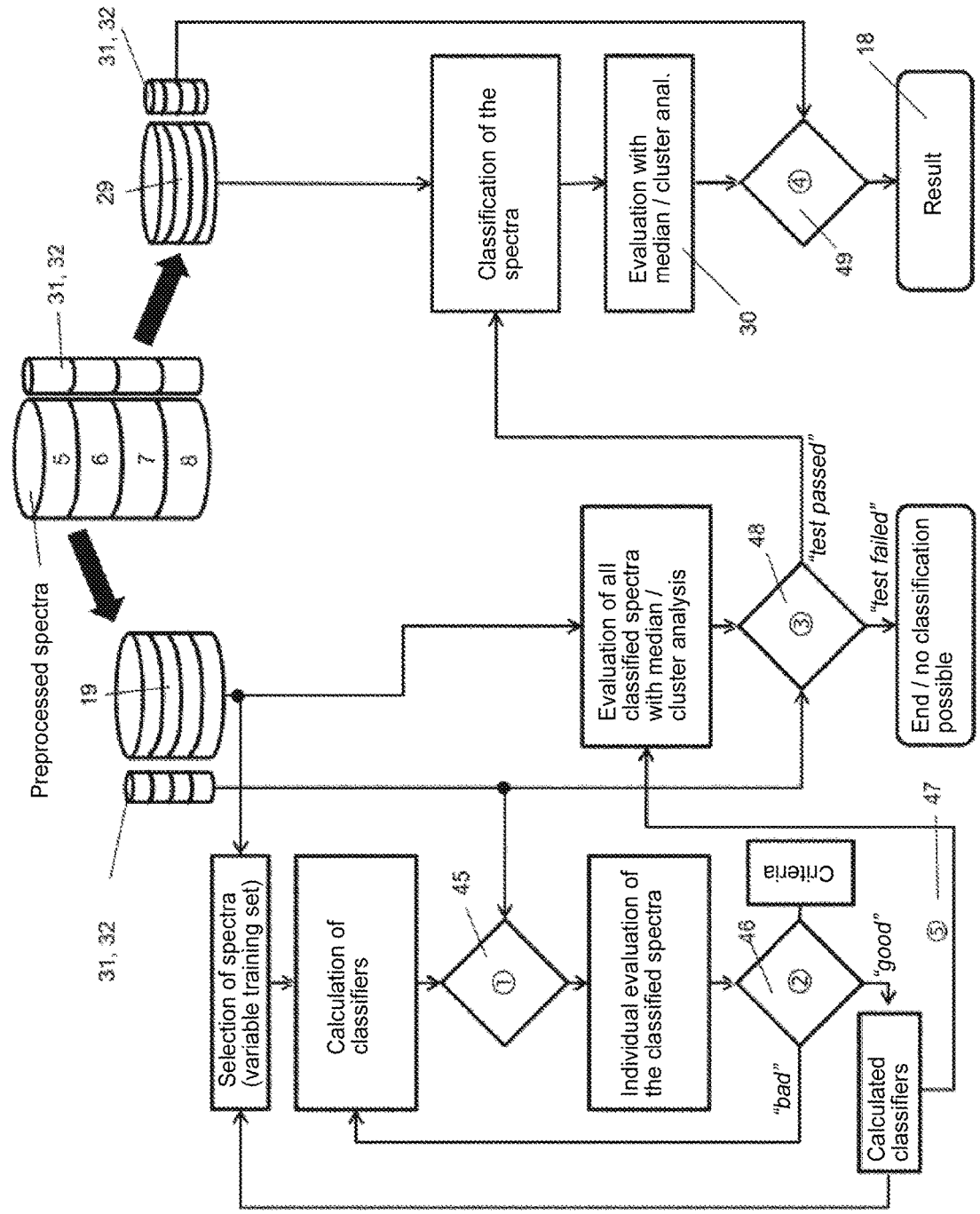

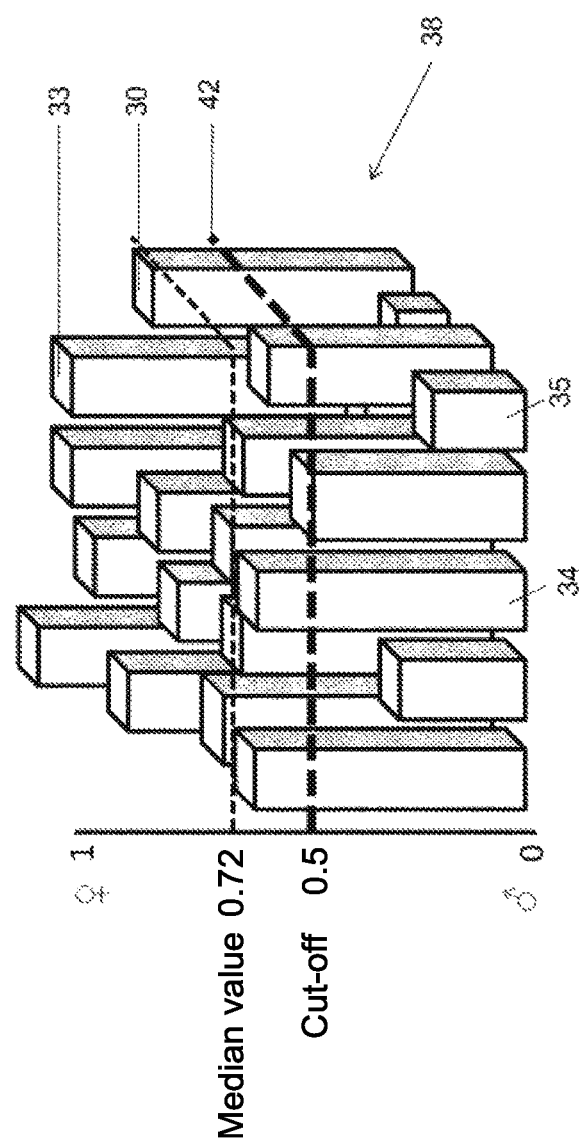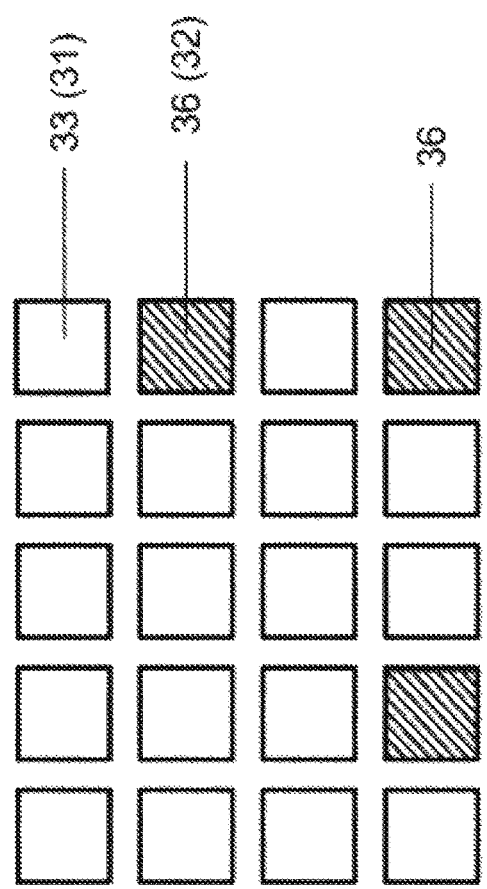

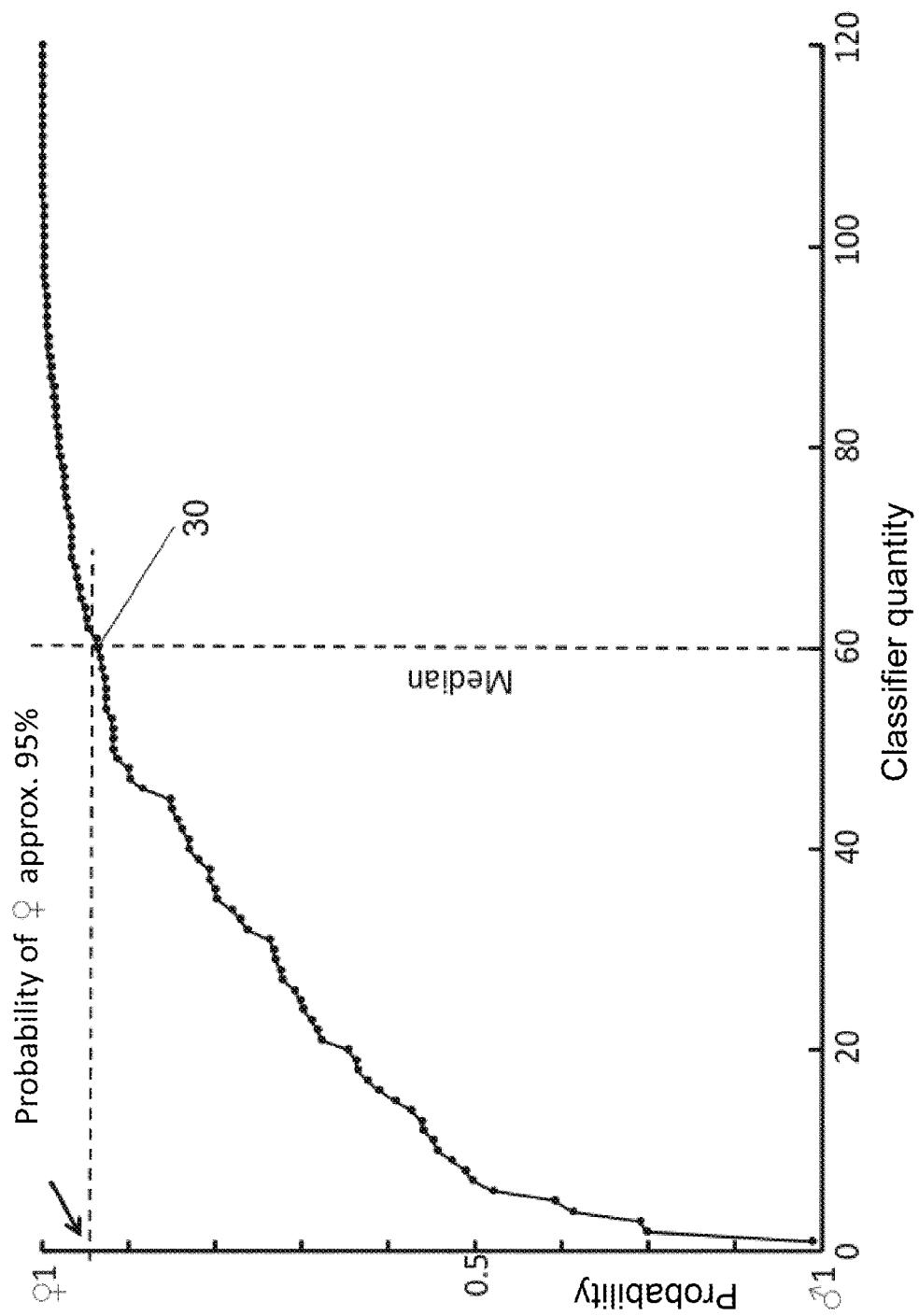

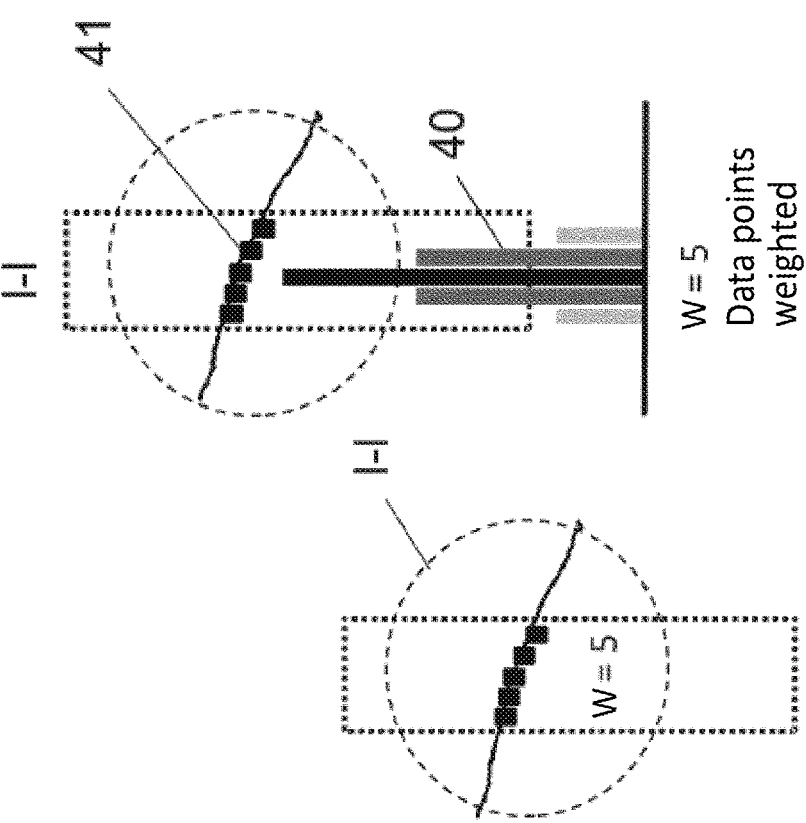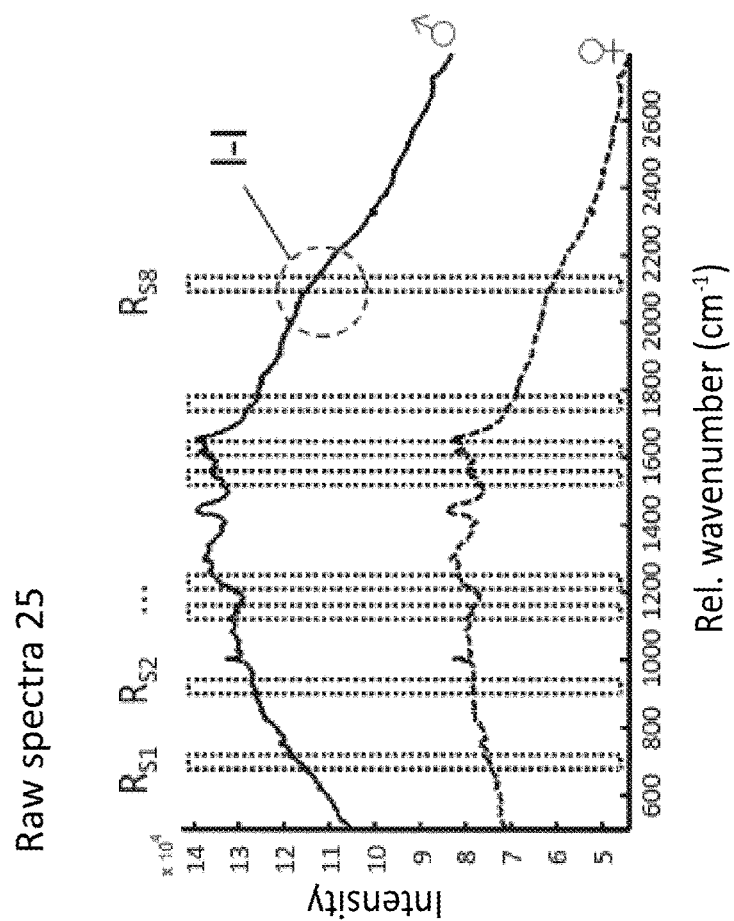
Fig. 10a
Fig. 10b
Fig. 10c

METHOD FOR CLASSIFYING SPECTRA OF OBJECTS HAVING COMPLEX INFORMATION CONTENT

BACKGROUND OF THE INVENTION
1. Field of the Invention

The invention relates to a method for classifying spectra of objects having complex information content with at least two different pieces of object information, in particular, optical molecular spectra, for assigning the object information.

2. Discussion of Background Information

Publications regarding methods for the supervised classification of optical spectra are known. These include, among others, the publication A. E. Nikulin, B. Dolenko, T., Bezabeh, R. L. Somorjai: Near-optimal region selection for feature space reduction: novel preprocessing methods for classifying MR spectra. NMR Biomed. 11 (4-5), 1998, p. 209-216; the publication B. K. Lavine, C. E. Davidson, A. J. Moores: Genetic algorithms for spectral pattern recognition, Vibrational Spectroscopy. Volume 28, Issue 1, 2002, pages 83-95, wherein the algorithm therein is based on the principal components and a weighting of spectral ranges is used for classification; and the publication J. Jacques, C. Bouveyron, S. Girard, O. Devos, L. Duponchel, C. Ruckebusch: Gaussian mixture models for the classification of high-dimensional vibrational spectroscopy data, Journal ofChemometrics, Volume 24, Issue 11-12, p. 719-727.

A method is described therein in which particularly high-dimensional spectral data are broken down into what are referred to as subspaces, which are subsequently classified by means of discriminant analysis.

Optical molecular spectra comprise a significant information content with regard to the molecular properties of the object being examined. Because of their high information density regarding the molecular structure, vibrational spectra in particular are considered to be a molecular fingerprint. In the spectroscopic analysis of complex biological objects, the information that is relevant according to the specification must be separated from the less significant or insignificant information and also from interference. For this purpose, chemometric methods are typically used, as well as multivariate methods in the case of higher-dimensional data.

If important spectral characteristics of the sought-after molecular object information are known, supervised classification methods can be used, as described, for example, in the publication G. Steiner, S. Kuchler, A. Herrmann, E. Koch, R. Saizer, G. Schackert, M. Kirsch: Cytometry, Part A 2008, 73A, 1158-1164.

The supervised classification methods are distinguished from other methods by a higher accuracy in the detection and quantitative evaluation of the sought-after information. In the known method of supervised classification according to FIG. 4a, a classifier 50 is calculated using a training set 19 that is composed of representative spectra with assigned properties. Then, with the aid of an independent test set 29, that is, the spectra are not used to construct the classifier 50, as is shown in FIG. 4a, the classifier 50 is checked for validation and evaluated and a classified test set 24 is obtained.

The construction of the classifier 50 by means of the training set 19 is verified using a test set 29 having, for example, maximally 30% of the spectra (dashed line to the created classifier) verified according to FIG. 4b, so that as a result a classified test set 24 (dashed line from the classifier 50 to the classified test set 24) is obtained.

A general problem with the supervised classification methods is the trade-off between the accuracy of the assignments obtained and the robustness of the classification. Often, very high accuracies can only be attained with what is referred to as an overtraining of the classifier. This is understood to mean that the classifier can only assign certain spectra correctly, wherein this occurs with very high accuracy. However, even the smallest deviations or disturbances lead to a dramatically reduced accuracy of the classification. Therefore, an accommodation between a best possible classification and high robustness of the classification is sought.

If spectra with very high variability are present, as is the case, for example, with in ovo spectra for determining the sex of chicken eggs, sacrifices in accuracy must inevitably be made for the preservation of adequate robustness of the classification. As a matter of principle, this intrinsic conflict cannot be solved. In order to nevertheless achieve a good stability with adequate accuracy, various methods for classification were newly developed in past years. The basic approach thereby is the parallelization of the classification via different decision trees. The Random Forest method is based on a network of uncorrelated decision trees, wherein the decision trees are grown or are linked through randomization during the training process. Each of the structures known as a tree makes one decision. The group of trees with the highest number of respectively identical decisions determines the result of the classification, that is, the assignment of the spectrum. However, the Random Forest method cannot react to different interferences or variations that occur in the spectra. Here, too, simply constructing too many trees can result in overtraining.

In the publication US20120321174 A1, a classification method based on the Random Forest method is described for image analysis. This supervised classification method is designed in particular so that small, but relevant characteristics are taken into consideration for the classification.

These relevant characteristics of the general classification method can, for example, also be defined and play a role in the in ovo spectroscopy of chicken eggs in the form of small spectrum-related signals for the sex information.

In the case of in ovo spectroscopy of chicken eggs, a respective supervised classification method is used to identify the sex.

However, optical in ovo spectra are often characterized by a very high natural variability that is clearly superimposed on the comparatively small signals for the sex information. There are also unavoidable external influences from the measurement environment itself.

Presently, the following different methods for classifying the spectra of objects, in particular for determining the sex of fertilized and/or incubated eggs, are specified in the publications cited below:

In the publication WO 2010/150265 A, a method based on a coloring, in particular of the feathers of the developed embryo, is described. The method is based on the fact that, in the advanced development stage (day 12 of incubation), the color of the feathers in certain chicken breeds allows a conclusion about the sex. The evaluation occurs using an algorithm for classification.

Additionally, in the publication WO 2014/021715 A2, a method is described in which the sex of the embryo is determined by means of endocrinological analysis.

The publication DE 10 2007 013 107 A1 describes the application of Raman spectroscopy for determining the sex of birds, wherein cell-containing material in general is examined. However, no method for in ovo sex determination is described.

The molecular spectra are recorded by means of methods and apparatuses according to the publications cited below:

A method and apparatuses for determining the sex of chicken eggs based on optical, preferably fiber-coupled, spectroscopy are described in the publication DE 10 2010 006 161 B3. However, no methods for analyzing the spectra and for classification are described.

In the publications DE 10 2014 010 150 A1 and WO 2016/000678 A1, methods and apparatuses for Raman spectroscopic in ovo sex determination are described. The evaluation of the spectra can advantageously take place using chemometric methods.

The publication EP 2 336 751 A1 describes a method for determining the sex of bird eggs. In the method, the germinal disc of an egg is illuminated with light and the emitted fluorescence is detected in a time-resolved manner. The identification of the sex occurs with the aid of supervised classification, wherein a classifier is calculated by means of the fractal dimension method.

In the publication U.S. Pat. No. 6,029,080 B, a method for in ovo sex determination is described. From the analysis of MRI images of the egg, the reproductive organs can be identified and used for the sex determination starting at a certain development stage of the embryo.

The disadvantage to the evaluation in these methods is that, ultimately, each of these methods uses a separate method for classifying spectra of objects with only one classifier.

Regarding the disadvantages, it should be noted in summary that, in order to still reliably extract the sought-after sex information from the recorded spectra, the use of only a single classifier is therefore not adequate to consider the detection reliability of the defined sex information adequate. Rather, the variable influences and the variations in the biochemical composition of the egg and also in the different development stages must be taken into consideration. To include this significant breadth of variation in a reliable detection method for classification, it is estimated that the calculation of only one classifier will therefore not be adequate.

SUMMARY

It is therefore the object of the invention to specify a method for classifying spectra of objects having complex information content, which method is suitably embodied so that a maximum accuracy of the determination of the assigned selected characteristics of objects is achieved, wherein at least the stability of the classification is also to be maintained. An accommodation between a best possible classification and high robustness of the classification is thus to be striven for. At the same time, an overtraining of the classifier is to be avoided.

The object is attained with the features of patent claim 1.

According to the characterizing part of patent claim 1, in the method for classifying spectra of objects having complex information content with at least two different pieces of object information, involving the use of a method for recording and preprocessing spectral data and a method, associated with the data preprocessing, for classification with the calculation of a classifier, a multiple classification method with at least two different data preprocessing methods for spectral data and a classification method assigned to the respective data preprocessing are performed after the recording of the spectra and the preprocessing of spectral data.

Within the scope of the invention, the recording of spectra is to be understood as meaning the acquisition, identification and storage of spectra and the generating of digitized signals for storage, which signals are available for further data preprocessing of the spectral data.

In the data preprocessing methods, depending on the preprocessing algorithm used, different corrected, preprocessed spectra are generated with numerous data points that are assigned to at least one method for classification.

The following steps are thereby carried out following recording and data preprocessing in the evaluation process for recorded spectra of objects:
- a calculation of multiple classifiers of series per type of data preprocessing;
- a determination of the classifiers of the series, iteratively calculated and validated;
- a calculation of probabilities for the class association;
- an equal incorporation of all classifiers of the series or classifiers into the determination of a classification result.

During the setting and determination of the number of calculated classifiers $N_G$ in the series for each classification group, both the scale of the spectral data points $v_S$ and the doubled half-width of the spectral regions $w_S$ and also the number of selected spectral regions $R_S$ for the classification are factored into an equation (I):

$$N_G = \frac{v_S}{2w_S \cdot R_S} \quad (I)$$

wherein with the equation (I) it is ensured that each data point $v_S$ can be selected with equal probability.

However, the data points belonging to a scale of the spectral data points can also be weighted.

At least one of the spectral preprocessing methods is structured such that respectively defined characteristics become prominent and other defined characteristics are suppressed, so that differently defined characteristics are used for the classification.

At least one spectral preprocessing method can be embodied with identically defined characteristics, and at least one of the aforementioned spectral preprocessing methods with differently defined characteristics can be used for the classification.

The preprocessed spectra can be configured as variable training sets, and multiple classifiers of the series or classifiers are iteratively determined and validated.

Within the scope of the invention, the classification is to be understood as meaning the placement, determined according to a predefined algorithm, of the preprocessed spectra in a respective class. The method for the classification is thereby carried out with the aid of predefined parameters, and the result of the classification is expressed by a calculated classifier.

At least one method of supervised classification and/or unsupervised classification can be used to select spectral regions or individual wavelength ranges and for subsequent analysis. A linear or non-linear discriminant analysis can thereby be used.

For the classification, neural network methods and/or a linear wavelet transform method can also be used.

The spectra from optical molecular spectroscopy, such as absorption, emission, scattering, or UV/vis, NIR, IR absorption, fluorescence or Raman, can thereby be classified.

As data preprocessing methods for the recorded spectral data or raw spectra, baseline corrections, normalizations, derivatives, covariance and/or a principal component analysis can be used.

For the evaluation of the classifiers of the series for a classification result, a calculation of a median or a performance of a cluster analysis can be provided.

The median or central value is thereby specified as a midpoint for distributions in statistics. The median of a list of numeric values is the value that is in the middle (central) position when the values are sorted by magnitude. The value of the magnitude in this case respectively represents the score of a classifier or the class association probability determined by the classifier.

In general, the method according to the invention can be completed with the following detailed steps:

- acquisition and recording of the spectra by means of at least one optical device having at least one spectrometer and/or additional detectors;
- generating digitized signals in the form of data points, and storing the recorded spectra in storage units of classification units of an evaluation unit;
- spectral preprocessing, in that the recorded and stored spectra are individually preprocessed in the individual storage units and the associated digitized evaluated signals are made available for further processing;
- separating the preprocessed spectra as a training set and as a test set;
- configuring and using the preprocessed spectra as a training set and a test set separate from the training set;
- wherein according to the invention at least a
- calculation of the classifiers of the series for the integrated individual classification methods, with an incorporation of iterative methods and a validation in the classification groups;
- classification of the preprocessed spectra of the training set with all classifiers of the series;
- placement of the spectra of the training set in a class of object information with an expression of a probability for the class association;
- calculation of a classification result by calculating the median or by performing a cluster analysis to show the probability result of the training set object information associated with a class;
- classification of the preprocessed spectra of the test set with all classifiers of the series;
- placement of the spectra of the test set in a class of object information with an expression of a probability for the class association; and
- calculation of the classification result by calculating the median or by performing a cluster analysis to show the probability result of the test set object information associated with a class are carried out.

All types of bird eggs, optionally chicken eggs, can be used as objects having object information, and in a special application case, the binary information about the female egg sex or about the male egg sex can be used as object information.

The method thus comprises steps for performing a multiple classification, based on different conventional evaluation methods, following a spectral preprocessing downstream of the spectral detection and recording, and following a subsequent repeated calculation of different classifiers. At least one spectral preprocessing method is thereby involved in which the spectral preprocessing is structured such that, if the equivalence of characteristics is factored in, an allowance for respectively defined characteristics also becomes more clearly prominent and other characteristics are more heavily suppressed. The spectra preprocessed in such a manner are then configured as a training set, wherein multiple series of classifiers are calculated. The classifiers are iteratively calculated and validated. Multiple classifiers can be determined in this manner. The spectra of the test set are then classified using all classifiers. The placement of the spectra in a defined class of object information/characteristics (for chickens: male, female) thereby preferably takes place as a score, or in an expression of a probability for the class association. To obtain a single statement from the classifiers, the relations among the classifiers are determined. For this purpose, a simple way of representing the relation is, for example, a calculation of the median or a cluster analysis.

An apparatus for classifying spectra of objects having complex information content, preferably with objects in the form of chicken eggs for a determination of binary egg information—female or male—wherein the aforementioned method is implemented in the apparatus, can at least comprise the following units:

- at least one optical detector having at least one spectrometer and/or additional detectors for the acquisition and recording of the spectra;
- a signal generator for generating digitized signals in a form of data points by which the spectra are manifested;
- storage units for storing the recorded spectra in the classification groups of an evaluator comprising the classification groups;
- units for spectral preprocessing spectral preprocessors in which the recorded spectra are individually preprocessed in the individual storage units and the associated digitized evaluated signals—the determined data points—are made available for further processing;
- training sets for configuring and using the preprocessed spectra;
- at least one classificationer for the classification groups calculating the classifiers of the series with an incorporation of iterative methods and a validation in the classification units;
- test sets for classifying the preprocessed spectra with all classifiers of the series;
- a placer for placing the preprocessed spectra in at least one binary class—for chickens: male or female—of object (egg) information with an expression of a probability for the class association;
- an evaluator to calculate the classification result in the form of the median or by means of performing a cluster analysis to determine the probability result of at least one piece of object (egg) information associated with the binary class—for chickens: female or male.

Developments and further embodiments of the invention are specified in the additional dependent claims.

BRIEF DESCRIPTION OF THE DRAWINGS

The invention is explained by means of exemplary embodiments with the aid of drawings.

Thereby:

FIG. 3a shows a schematic illustration of the spectra assigned to the raw spectrum classification method according to FIG. 2a, wherein the dotted-line spectrum is assigned to the female chicken-egg spectrum;

FIG. 3b shows a schematic illustration of the spectra assigned to the linear baseline correction classification method according to FIG. 2b, wherein the dotted-line spectrum is assigned to the female chicken-egg spectrum;

FIG. 3c shows a schematic illustration of the spectra assigned to the normalization classification method according to FIG. 2c, wherein the dotted-line spectrum is assigned to the female chicken-egg spectrum;

FIG. 3d shows a schematic illustration of the spectra assigned to the Raman spectrum classification method according to FIG. 2d, wherein the dotted-line spectrum is assigned to the female chicken-egg spectrum;

FIG. 4b shows a flowchart for the multiple classification method according to the invention having a training set and test set in an algorithmic connection, with classification-result designing from a large number of classifiers;

FIG. 5 shows a schematic illustration of a probability/classifier quantity bar graph for twenty classifiers according to FIG. 1 for a chicken egg used as an example, wherein the bars located above the dashed line—cut-off—are assigned to the female sex;

FIG. 6 shows a top view of the bar graph for an egg according to FIG. 5 and a possible view on a display;

FIG. 9 shows a graph of the calculated median, illustrated as a dashed line, for an egg detected as female with the 120 classifiers according to FIG. 8 in a probability/classifier quantity graph.

FIG. 10a shows a schematic illustration of an individual classification method with spectral preprocessing: raw spectra, wherein all characteristics are incorporated equally, with eight selected spectral regions $R_{S1}$ to $R_{S8}$ for a scale of the spectral data points over the entire spectral range between the wavenumbers 570 $cm^{-1}$ and 2750 $cm^{-1}$ for determining the number of classifiers per data preprocessing.

FIG. 10b shows an enlarged section (I-I) of the data point graph in the predefined spectral region $R_{S8}$ according to FIG. 10a;

FIG. 10c shows an enlarged section (I-I) of the data point graph in the spectral region $R_{S8}$ with a specification of the weighting of data points in the range of the region $R_{S8}$ according to FIG. 10a and FIG. 10b;

DETAILED DESCRIPTION

FIG. 1 and FIGS. 2a, 2b, 2c, 2d are considered together below.

Figure 1:
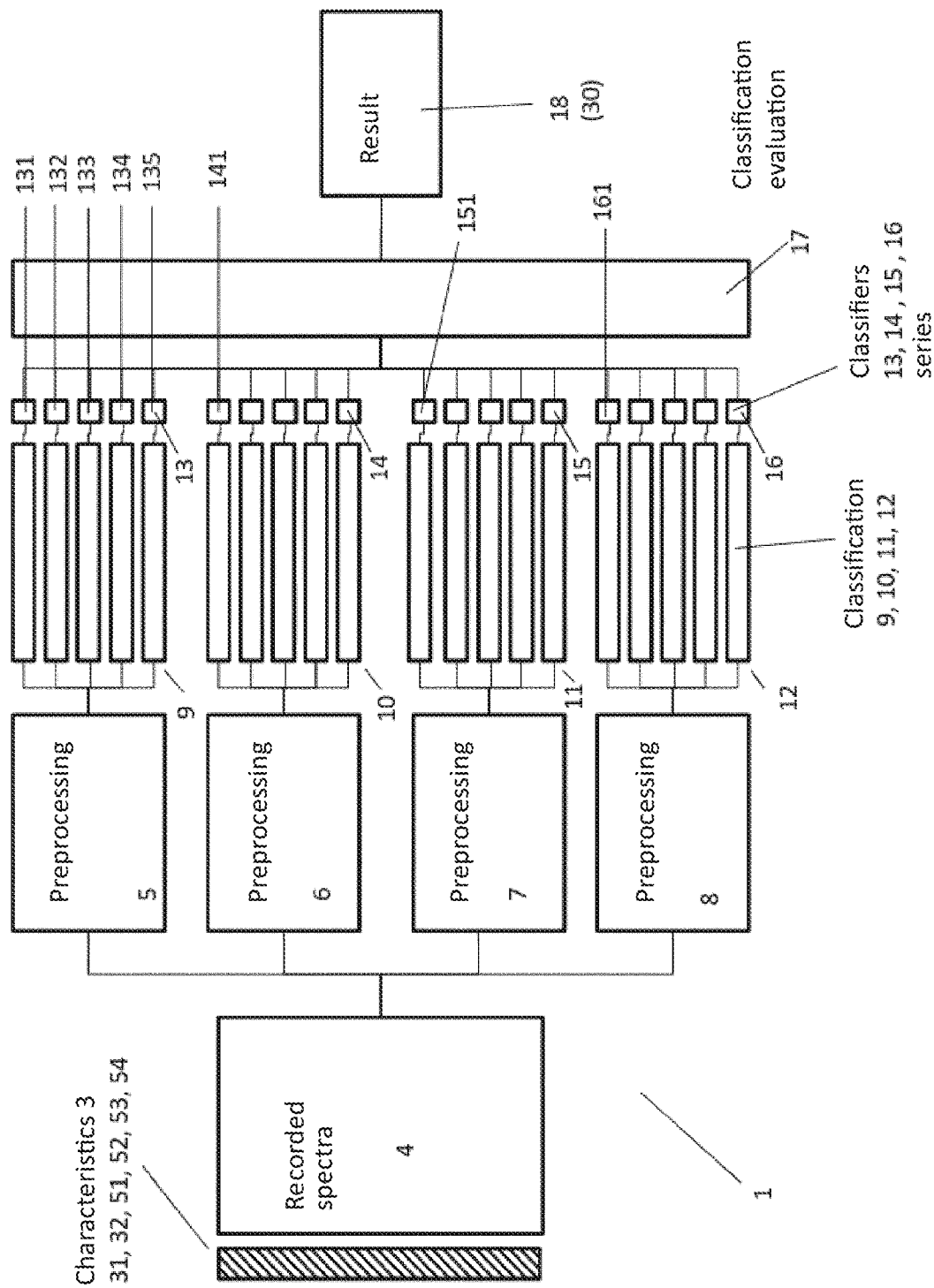
FIG. 1 shows a schematic block diagram of a method according to the invention for classifying spectra of objects having complex information content, in particular optical molecular spectra, for assigning and determining binary object information, wherein the method is embodied as a multiple classification method.

FIG. 1 shows, in a schematic block diagram, a method 1 according to the invention for classifying spectra 4 of an object 2 having complex information content with at least two/binary and different pieces of object information/characteristics, in particular optical molecular spectra 4, for assigning object information/characteristics 3 for a probabilistic definition, for example, of binary object information 31, 32.

Bird eggs, for example chicken eggs, can be used as the objects 2 being examined, and the characteristic 31 for the female egg sex and the characteristic 32 for the male egg sex, for example, can be searched for and defined as binary object information 3.

The method 1 according to the invention for carrying out the classification is described below.

For this purpose, a block-wise sequence of the method 1 according to the invention is shown in FIG. 1.

In the method 1 for classifying spectra 4 of objects 2 having complex information content with at least two different pieces of object information, the calculation of a classifier occurs after the recording, involving the use of a method for preprocessing data and a method, associated with the data preprocessing, for classification.

According to the invention, following the recording and data preprocessing of spectra 4, a multiple classification method with at least two different methods of data preprocessing 5, 6, 7, 8 of the spectra 4 and the method, assigned to the respective data preprocessing 5, 6, 7, 8, for classification in the groups 9, 10, 11, 12 is carried out to determine multiple, for example five, classifiers per group 9, 10, 11, 12, that is, a large number of classifiers overall, for example twenty (five classifiers/group×four groups) classifiers 131, 132, 133, 134, 135, etc., for the series 14, 15, 16.

The following steps are thereby carried out following recording and data preprocessing of the spectra, wherein the steps refer to FIG. 1:
- a calculation of five classifiers of the series 13, 14, 15, 16 per type of data preprocessing 5, 6, 7, 8 so that ultimately twenty classifiers 131, 132, 133, 134, 135, etc. are determined;
- a determination of the five classifiers of the series 13, 14, 15, 16, iteratively adjusted and validated;
- a calculation of probabilities for the class association;
- an equal incorporation of all five classifiers of the series 13, 14, 15, 16 and/or classifiers 131, 132, 133, 134, 135, etc. into the determination of a classification result 18, for example, in the form of a median 30.

During the setting and/or determination of the number of classifiers $N_G$ to be calculated in the series 13, 14, 15, 16 in relation to the groups 9, 10, 11, 12, a scale of the spectral data points $v_S$ and a doubled half-width $w_S$ of spectral regions $R_S$ and also a number of selected spectral regions $R_S$ are factored into the following equation (I):

$$N_G = \frac{v_S}{2w_S \cdot R_S} \quad (I)$$

wherein with the equation (I) it is ensured that each data point $v_S$ can be selected with equal probability.

Figure 7:
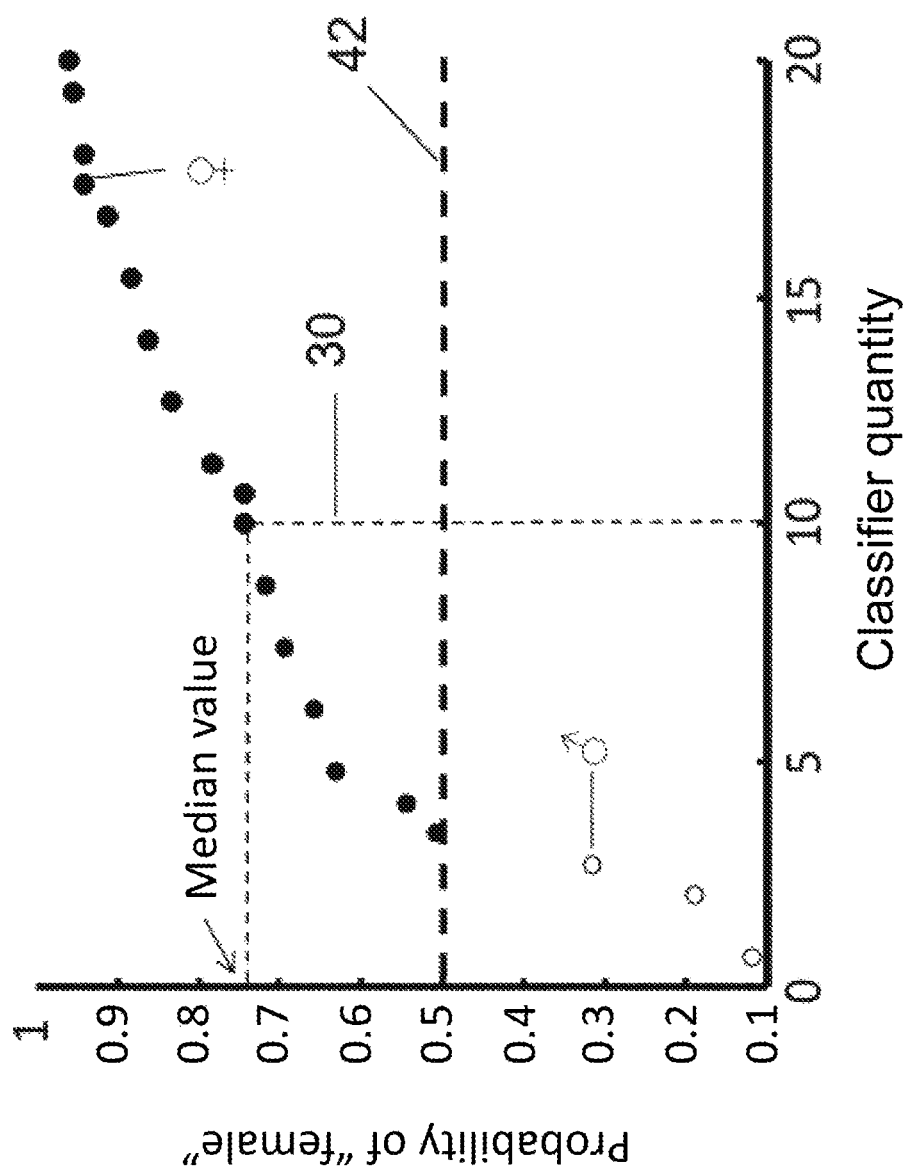
FIG. 7 shows a probability (female)/classifier quantity graph with the specification of the calculated median for an egg with the 20 classifiers according to FIG. 6, wherein a cut-off with a thick dashed line is at 0.5 for the probability and a median value with a thin dashed line is at approximately 0.72 for the probability for "female." so that the sex of the egg can be identified as female.

For a total of twenty classifiers of the four series 13, 14, 15, 16 with $N_G$ (13), $N_G$ (14), $N_G$ (15), and $N_G$ (16) according to FIG. 1 and according to FIG. 5, FIG. 6, and FIG. 7, the following parameters, for example, are predefined for the entire spectral range from 500 cm$^{-1}$ to 2750 cm$^{-1}$.

Scope of the spectral data points $v_S$ in a predefined total spectral range of 500 cm$^{-1}$ to 2750 cm$^{-1}$ with $v_S$=800;
Number of selected spectral regions $R_S$ with $R_S$=8;
Width W of the spectral regions $R_S$ with W=2·$w_S$=5, that is, there can be twenty data points $v_S$ in one region $R_S$. The half-width $w_S$ is therefore $w_S$=2.5.

Figure 2A:
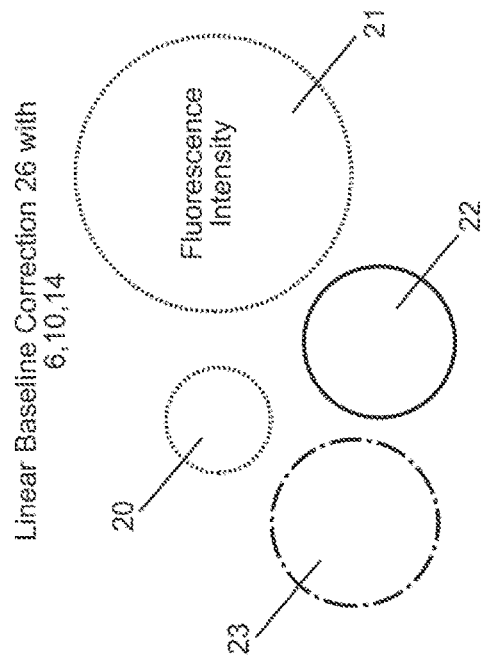
FIG. 2a shows a schematic illustration of an individual classification method with spectral preprocessing: raw spectra, wherein all characteristics are incorporated equally (equally-sized circles)
Figure 2B:
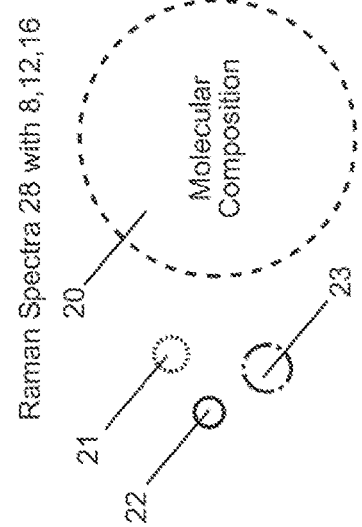
FIG. 2b shows a schematic illustration of an individual classification method with spectral preprocessing: linear baseline correction, with a favored, large characteristic circle for the fluorescence intensity and multiple less relevant, small characteristic circles.
Figure 2C:
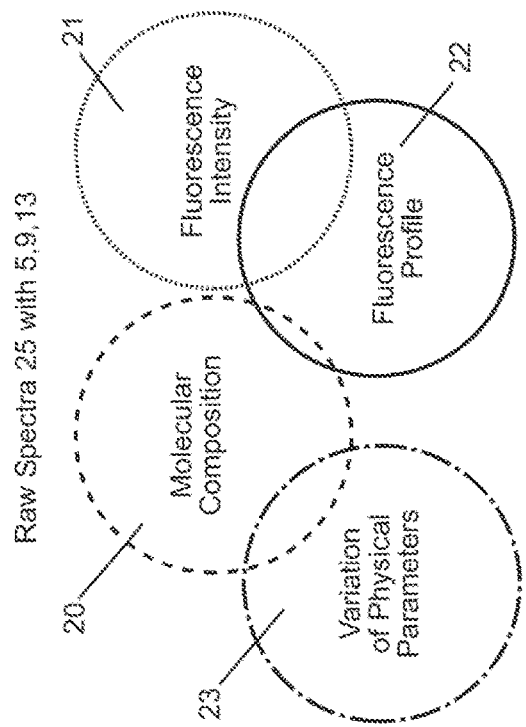
FIG. 2c shows a schematic illustration of an individual classification method with spectral preprocessing: normalization, with a favored, large characteristic circle for the fluorescence profile and multiple less relevant, small characteristic circles.
Figure 2D:
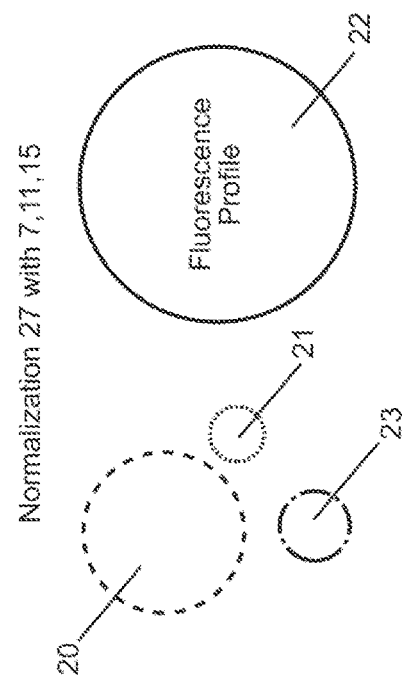
FIG. 2d shows a schematic illustration of an individual classification method with spectral preprocessing: Raman spectra, with a favored, large characteristic circle for the molecular composition and multiple less relevant, small characteristic circles.

According to FIGS. 2b, 2c, 2d, the spectral preprocessing methods 6, 7, 8 can be structured such that respectively defined characteristics are favored and become prominent, and other characteristics are suppressed.

In the spectral preprocessing 5 of the raw spectra 25 according to FIG. 2a, all incorporated characteristics can be treated and preprocessed in an equal manner.

Figure 4A:
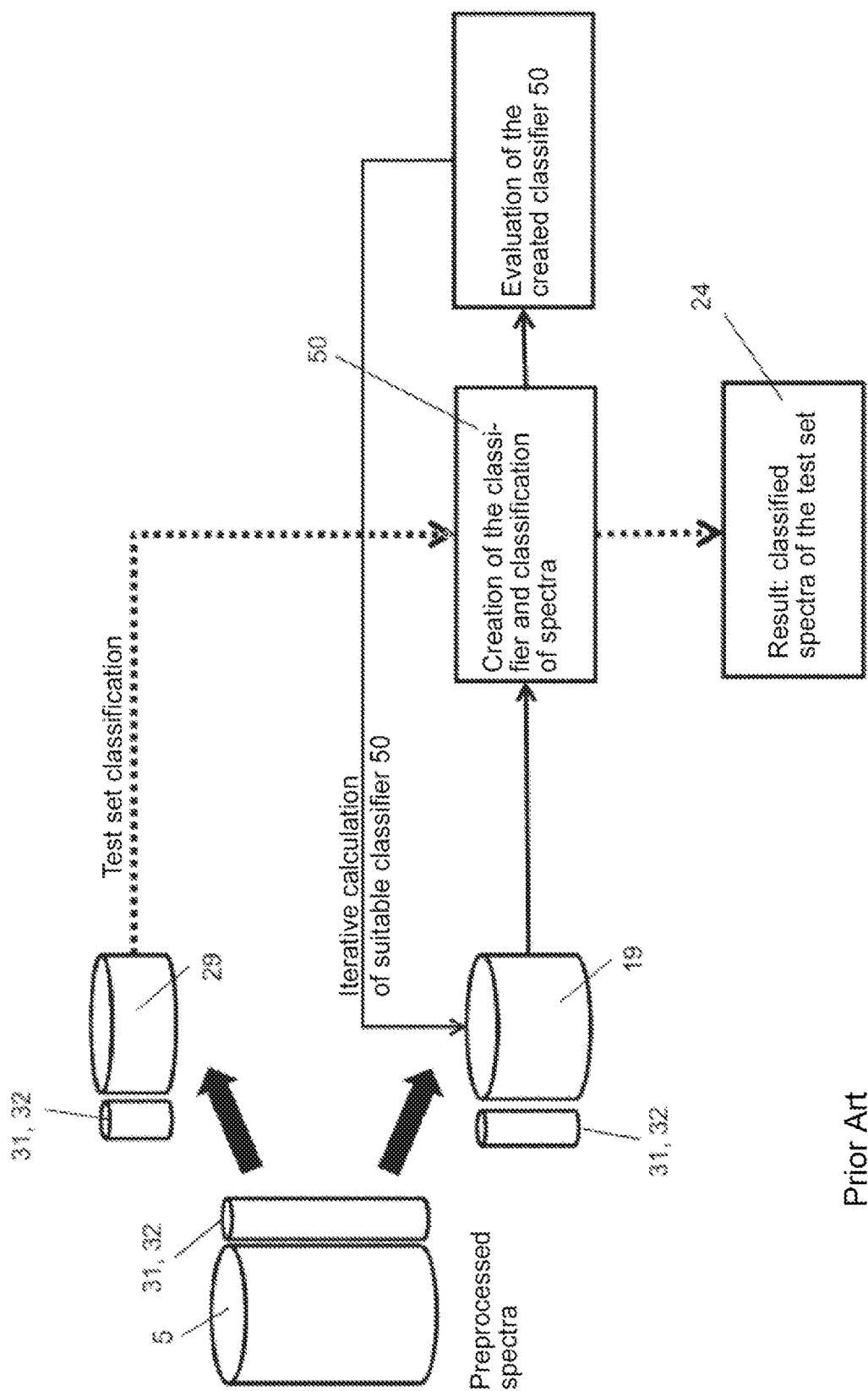
FIG. 4a shows a schematic illustration of the sequence of a classification with determination of a classifier according to the prior art.

The preprocessed spectra 4 are configured as a training set 24 according to FIG. 4b, and multiple classifiers of the series 13, 14, 15, 16, or for example the classifiers 131, 132, 133, 134, 135 specifically for series 13 etc., are iteratively determined and validated.

After passing through at least two classification methods 9, 10, 11, 12, each provided with a preceding data preprocessing 5, 6, 7, 8 using different spectra, with at least one determined classifier 131, 141, 151, 161, according to FIG. 1 at least two of the determined classifiers 131, 141, 151, 161 can be collectively obtained and used for the evaluation and the subsequent determination of a probability result 18 with regard to the predefined different pieces of object information 31, 32, wherein the probability result 18 is outputted so that a conclusion at least about the object information 31 or 32 determined to have a highest value is rendered possible.

At least one method of supervised classification and/or unsupervised classification can be used to select spectral regions $R_S$ or individual wavelength ranges/wavenumber ranges and for subsequent analysis.

The subsequent analysis can be a linear discriminant analysis or a non-linear discriminant analysis.

However, a neural network method and/or a linear wavelet transform method can also be used as a method for classification in the groups 9, 10, 11, 12.

The spectra 4 from optical molecular spectroscopy, such as absorption, emission, scattering, or UV/vis, NIR, IR absorption, fluorescence, Raman, can be classified using the method according to the invention.

For the data preprocessing methods 5, 6, 7, 8 shown in FIG. 1 raw spectra 25, baseline corrections 26, normalizations 27, derivatives, covariance, and/or a principal component analysis/Raman spectra 28 can be defined and used. A data preprocessing is constituted by the formation of digital signals, that is, of data points, which when strung together result in the respective calculated spectral curve of 25, 26, 27, 28, and which can thus be assigned to the different individual classification methods used.

For the evaluation of the classifiers of the series 13, 14, 15, 16 for a classification result 18, a calculation of a median 30 (FIG. 7, FIG. 9, FIG. 11a) for an object 2 or performance (FIG. 11a, FIG. 11b) of a cluster analysis can be provided.

Figure 11A:
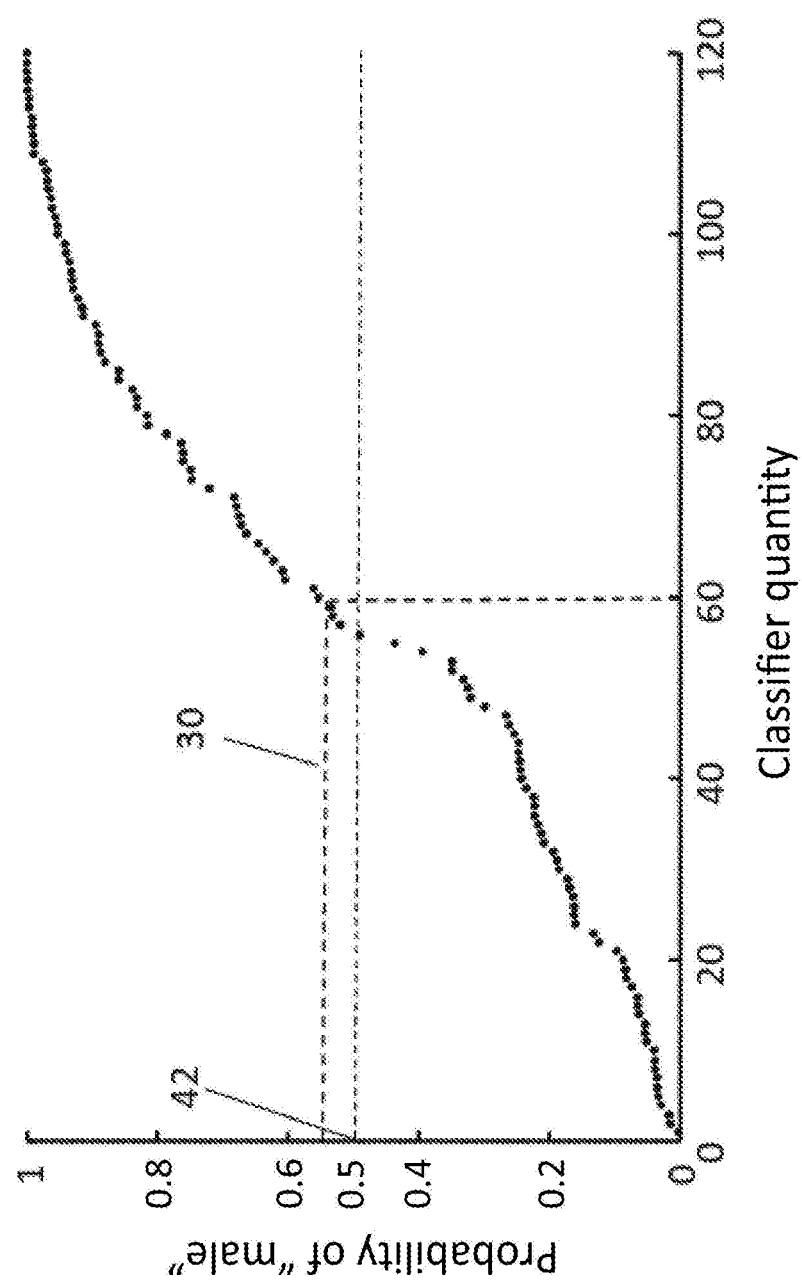
FIG. 11a shows a graph of the calculated median, illustrated as a dashed line, for an egg detected as male with the 120 classifiers similar to FIG. 8 in a probability/classifier quantity graph.

The known k-means cluster analysis can be used as an example of an evaluation. In FIG. 11a, at least two clusters are thereby predefined for "male" and "female." The cluster to which the most elements, that is, probabilities, are assigned, defines the sex (FIG. 11b—male). A group of compiled elements with similar properties (here: probabilities—classification results) is referred to as a cluster.

FIG. 11 a shows a curve of the interdependency between the probability for a "male" characteristic and a classifier quantity of 120 classifiers. In the plot of the sorted probabilities, it is apparent that the median 30 lies just above the cut-off 42 of 0.5 on the probability coordinate. The egg 2 is therefore just barely classified as male. The known k-means cluster analysis leads to a clearer result in this case.

Figure 11C:
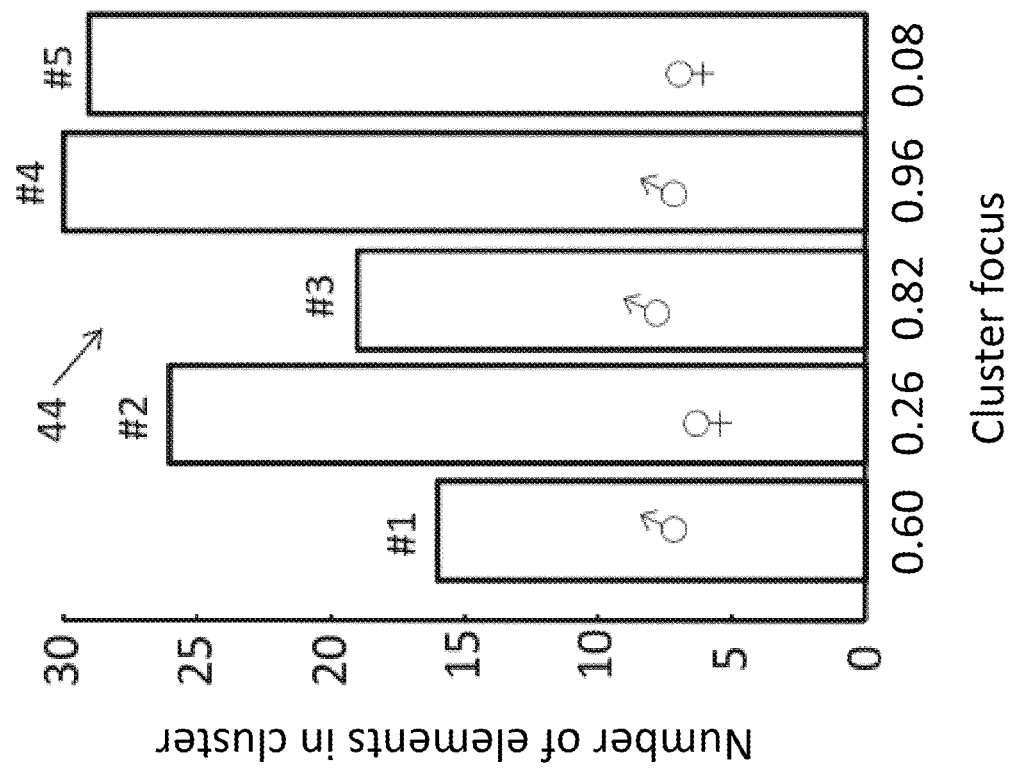
FIG. 11c shows a second histogram illustration of the interdependency of the number of elements in the cluster and the focus of the cluster.
Figure 11B:
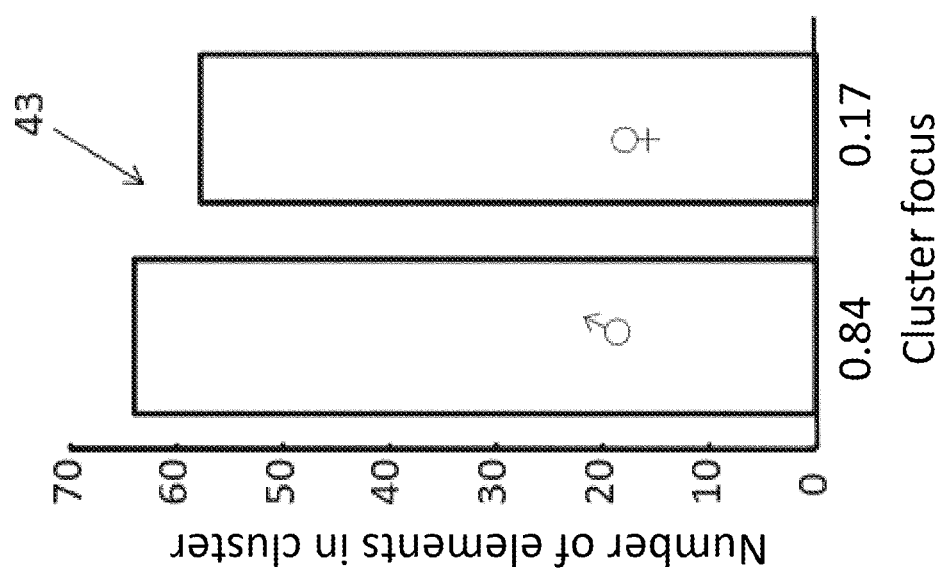
FIG. 11b shows a first histogram illustration of the interdependency of the number of elements in the cluster and the focus of the cluster.

For this purpose, FIG. 11b shows a first histogram illustration 43 of the interdependency between the number of elements in the cluster and the focus of the cluster, and FIG. 11c shows a second histogram illustration 44 of the interdependency between the number of elements in the cluster and the focus of the cluster, wherein the obtained classification results are regarded as elements.

To this end, two clusters are formed in FIG. 11 b, the foci of which are 0.84 and 0.17. Because more elements, that is, classification results, are assigned to the cluster with the focus of 0.84, the egg 2 can be evaluated as being clearly male.

If five clusters an: selected in the histogram illustration 44 according to FIG. 11c, this result is also confirmed. Here, 65 calculated probability values are classified as male, wherein the cluster (number 4=#4) with the strongest value of 0.96 for "male" also contains the most elements according to FIG. 11a. The sex of the egg 2 is therefore clearly "male."

This also applies equally and similarly for the cluster analysis if the sex of the egg 2 is determined to be female.

The method 1 according to the invention can be achieved by means of the following steps, with the use of hardware components of an accompanying apparatus:
- acquisition and recording of the spectra 4 by means of at least one optical device having at least one spectrometer and/or additional detectors;
- generating digitized signals, the data points, and storing the detected spectra 4 in storage units of the classification units of an evaluation unit;

spectral preprocessing 5, 6, 7, 8, in that the stored spectra 4 composed of the data points $v_S$ are individually evaluated in the individual storage units and the associated digitized evaluated signals are made available for further processing;

configuring or forming the pretreated spectra 25, 26, 27, 28 as a training set 19 and a test set 29 separate therefrom;

calculating the classifiers of the series 13, 14, 15, 16 in the form of individual classifiers 131, 132, 133, 134, 135 of a series 13, etc. of the integrated individual classification methods 9, 10, 11, 12, with an incorporation of iterative methods and a validation in the classification units/groups;

classifying the evaluated spectra 25, 26, 27, 28 of the test set 24 with all classifiers of the series 13, 14, 15, 16;

placing the spectra 25, 26, 27, 28 in a class of object information with an expression of a probability for the class association;

calculating the median 30 or performing a previously indicated cluster analysis to show the probability result in the form of a classification result 18 of a piece of object information associated with a class.

The construction of classifiers with regard to the series 13, 14, 15, 16 by means of the training set 19 is verified using a test set 29 having, for example, maximally 30% of the spectra (dashed line to the classifiers 13, 14, 15, 16) according to FIG. 4b, so that a classified test set 24 (dashed line from the classifiers of the series 13, 14, 15, 16 to the classified test set 24) is obtained as a result.

It should also be noted that, by their very nature, the recorded in ovo spectra 4 are generally highly variable. This is caused on the one hand by the inherent variability of biological systems and on the other hand by the sensitivity of Raman spectroscopic measurements.

External interference of a systematic and random nature results in a high variability of the spectral characteristics and is thus superimposed on the sex-relevant information.

Furthermore, in the method of Raman spectroscopy, fluorescent light is also present which likewise contains molecular information, but which is also superimposed on the normally much weaker Raman spectroscopic molecular information about the composition of the examined object.

In FIG. 2a, a schematic illustration of the raw spectra 25 is shown as one of all integrated individual classification methods in FIG. 1 for the four individual classification methods.

According to FIG. 2a, FIG. 2b, FIG. 2c, and FIG. 2d, at least four classes of signals or defined characteristics can generally be formed:
  molecular composition 20,
  fluorescence intensity 21,
  fluorescence profile 22, and
  variation of physical parameters 23,
wherein these defined characteristics 20, 21, 22, 23 are embodied as equally sized, outlined circles and/or circles with differently dashed outlines for the purpose of visual illustration in FIG. 3a, FIG. 3b, FIG. 3c, and FIG. 3d.

Underlying the classifiers is one mathematical expression each for separating the signals according to the object information 3 (31 female, 32 male).

Three classes/characteristics 20, 21, 22 of the four classes/characteristics 20, 21, 22, 23 contain sex-relevant information. However, it is not possible to eliminate the variation 23 of the physical parameters from the spectra 4 in such a way that no or only a minor loss of information occurs in the three other classes 20, 21, 22. Thus, because of the equivalence of all of the defined characteristics, the raw spectra 25 have the highest content of all information, but also the highest content of interference. By adding at least one of the indicated data preprocessing methods, for example 26, from the data preprocessing methods 26, 27, 28 with differently evaluated characteristics, the interference is reduced. By using additional data preprocessing methods 27, 28, the original interference is minimized or even eliminated.

FIG. 2b shows that the in ovo spectra 4 recorded as digital signals are subjected to a linear baseline correction 26, wherein the fluorescence intensity signal 21 (large circle) stands out. At the same time, signals 23 for physical parameters in the spectra are suppressed (small circle). Due to the typically significant intensity differences between fluorescence signals and Raman signals, the information about the molecular composition 20 (small circle) recedes into the background. However, the fluorescence intensity 21 (large circle) itself is potential marker for the sex detection, since male embryos frequently, but not always, exhibit a biochemical blood composition that has a higher fluorescence intensity 21 than female embryos or the blood of female embryos.

FIG. 2c shows that, by means of the method of spectral normalization 27, for example by means of vector normalization or area normalization, variations in the fluorescence intensity 21 (small circle) can be compensated for and the random influences of physical parameters 23 (small circle) can be minimized. This preferably allows the fluorescence profile 22 (large circle) to be emphasized. At the same time, only a few pieces of information for the molecular composition 20 (small circle), based on the Raman signals, are minimized. Since the fluorescence profile 22, that is, the spectral characteristics of the fluorescence, is determined by the molecular composition 20, sex-relevant information can be emphasized.

FIG. 2d shows that a most complete possible correction of what is referred to as the background of Raman spectra 28 results in an exclusive emphasis on the Raman bands, that is, on the information about the molecular structure and composition 20 (large circle) of the examined object 2.

In FIGS. 3a, 3b, 3c, and 3d, one schematic illustration each of the spectra assigned to the individual classification methods (based on the relative wavenumber) is shown in reference to FIGS. 2a, 2b, 2c, 2d.

At least the spectral preprocessing method 5 with equivalently defined characteristics is added to at least one of the spectra preprocessing methods 6, 7, 8 with differently defined characteristics for the purpose of evaluation.

FIG. 4b shows a flowchart for the multiple classification method according to the invention having a training set and test set in local separation, but in an algorithmic connection, with a classification-result design from a large number of classifiers. The respective spectral preprocessing is thereby structured thereby such that respectively defined characteristics become more clearly prominent and other characteristics are more strongly suppressed. The spectra 4 preprocessed in such a manner are, according to FIG. 4b, then configured as a variable training set 19, wherein multiple series 13, 14, 15, 16 of classifiers, for example specifically in one series 131, 132, 133, 134, 135, etc., are calculated. Typically, all classifiers of the series 13, 14, 15, 16 are iteratively calculated and validated. Variability means that, without additional preprocessing methods, any desired spectra can be selected for each classifier being calculated. In this manner, multiple classifiers 131, 132, 133, 134, 135 can for example be defined for the first series 13, etc. This also applies for the other series 14, 15, 16. According to FIG. 4b, the selected spectra of the test set 29, for example 30%, are subsequently classified to form a classified test set 24 using all classifiers. The placement of the spectra 4; 25, 26, 27, 28 in a defined class of characteristics (male, female) thereby preferably takes place as a score, or in an expression of a probability for the class association. To obtain a single statement from the classifiers of the series 13, 14, 15, 16 or 131, 132 133, 134, 135, etc., the relations among the classifiers 13, 14, 15, 16; 131, 132, 133, 134, 135 are determined. A simple way of doing so is the calculation of the median 30 or, as stated previously for example, the performance of a cluster analysis.

In the flow chart illustrated in FIG. 4b, a comparison of each classified spectrum from each form of preprocessing with the characteristic takes place in the node provided with the reference numeral 45=①. The result is thereby only outputted as "true" or "false."

Example

The training set 19 comprises 100 spectra. Of these, 60 are selected for the calculation of the classifiers. If four methods of data preprocessing 5, 6, 7, 8 are used, there are 60×4=240 classified spectra. From the comparison with the list of characteristics there thus result 240 statements of either "true" or "false." This result is, for example, achieved in the set 129th iteration step.

In the node designated by the reference character 46=②, an evaluation of the classified spectra takes place with regard to a set criterion or multiple set criteria. An accuracy bound or a maximum number of iterative steps, for example, serve as criteria. The criteria can linked by an AND or OR logical operation.

Example: Of the 240 possible statements. 205 are "true" and 35 are "false." There thus results a correctness of 85% for the training set.

Before the classification begins, the following are set as criteria:
 1. correctness >80% and
 2. a maximum number of iterations: 1000.
That is, after the completed
 129th iteration step <1000
 and with
an obtained correctness of 85%>predefined correctness.

In the case of a logical AND operation, it is possible to arrive at "bad" (wherein the classifiers are stored as a best intermediate result, however) and in the case of a logical OR operation at "good."

If the number of the predefined classifiers being defined has been reached at the junction indicated by the reference character 47=⑤, all classifiers (each of which has namely led to the best result at node ②=45) are passed to the validation of the entire training set 19.

Example: It is predefined that 30 classifiers per data preprocessing 5, 6, 7, 8 are to be calculated and result in a multiple classification. Thus, 30×4=120 classifiers are passed to validation.

At the node/comparison junction indicated by the reference character 48=③, a collective evaluation of the classification of all spectra in the training set 19 takes place according to the leave-one-out or cross-validation method.

In the event of a "passed test." the classifiers are passed to the classification of the "unknown" spectra of the test set 29.

If the test is not passed, a classification according to the predefined criteria is not possible.

At the node/comparison junction indicated by the reference character 49=④, a final evaluation of the classification of the spectra in the test set 24 is performed with the aid of the known characteristics of the spectra.

Example

The test set 29 comprises 50 spectra. These spectra were respectively classified with 120 classifiers, that is, 120 probabilities for the class association are assigned to each spectrum. From this, the association with a class follows according the median or cluster analysis. This is the result of the multiple classification for each individual spectrum. If, for example, 41 of the 50 spectra are correctly classified, this results in a correctness of 82% for the entire test set 24.

From the comparison with the list of characteristics, the method 1 of multiple classification created in such a manner is conclusively evaluated. The method is thus created and can then be used for spectra without knowledge of the characteristics.

FIG. 5 shows a schematic illustration of a probability/classifier quantity bar graph 38 for 20 classifiers according to FIG. 1 for displaying an egg 2 identified as female. The unshaded end regions/front faces 33 of bars 34 can thereby be associated with the female sex above a certain line—the cut-off 42—and the bars 35 with the shaded end regions/front faces 36 can be associated with the male sex below the cut-off 42. In FIG. 5, the cut-off value is at 0.5 and the median 30 therein has a value of 0.72. Therefore, the egg 2 is clearly classified as "female."

FIG. 6 shows the top view related to the perspective bar graph, which view is shown on a color display as a classification result image 37 with the majority of unshaded end regions/front faces 33 for the "female" object information 31. On the color display, the unshaded front faces 33 can be embodied in red and the shaded front faces 36 can be embodied in blue, so that a color visual display of the evaluation of the sex can also be made.

The shaded squares can thereby be depicted in a blue color and the unshaded squares in a red color. The few blew squares indicate the male object information 32. The more numerous red squares indicate the female object information 31. Since the red squares are more numerous, the sex of the incubated chicken egg 2 can be identified as a female characteristic 31.

FIG. 7 shows an illustration of the calculated median 30 at 10 classifiers in relation to the quantity of the twenty classifiers for an egg 2 according to FIG. 1, with a series of five classifiers 131, 132, 133, 134, 135 each per group for four groups 9, 10, 11, 12. In the bar graph and median illustration, 17 classifiers thereby result in the display of a female egg 2. The overall classification result 18 can be stated using the calculated median 30.

Figure 8:
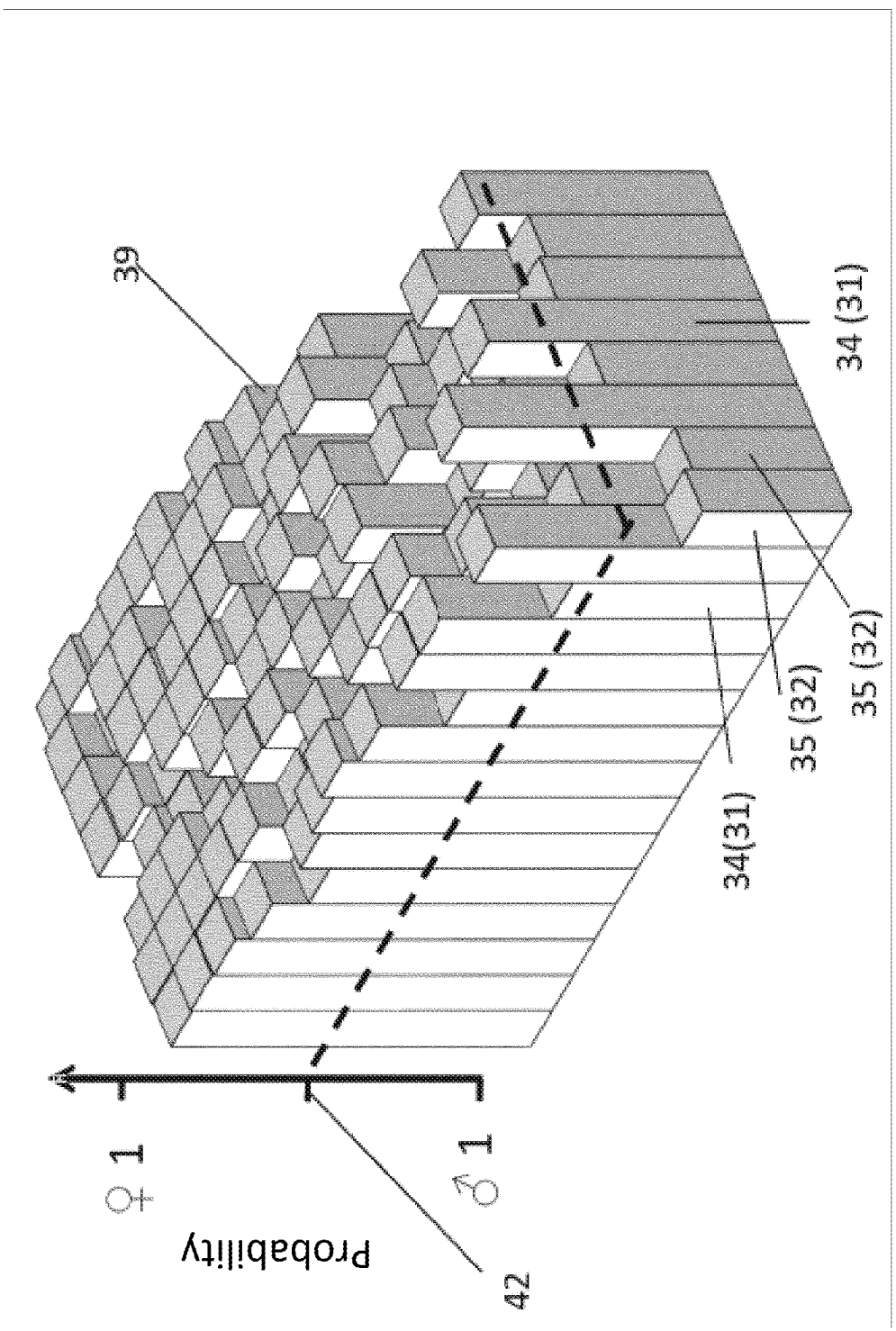
FIG. 8 shows a schematic illustration of a probability/classifier quantity bar graph for an egg for optionally 120 classifiers, wherein the end regions of the bars located above the thick dashed line—cut-off—are assigned to the female sex of an egg and the end regions of the bars located below the thick dashed cut-off are assigned to the male sex of an egg.

FIG. 8 shows a schematic illustration of an additional exemplary probability/classifier quantity bar graph 39 for 120 classifiers, illustrated as bars, for the display of an egg 2 identified as female. The cut-off 42 once again shows the boundary between the "male" characteristic and the "female" characteristic. Here, too, the bars 34 (31) ending above the cut-off 42 are shown unshaded on their front faces, and the bars 35 (32) ending below the cut-off 42 are shown shaded.

For an egg 2 with a male sex characteristic 32, a different bar graph can be embodied, wherein in this case the front faces located above the cut-off 42 of the embodied bars 35, being in the majority compared to the unshaded front faces of the bars 34, are shaded (not shown).

FIG. 9 shows an illustration of the calculated median 30 in relation to the quantity of 120 total classifiers according to the bar graph in FIG. 8 in a probability/classifier quantity graph for an egg 2 with a female sex characteristic 31, with classifiers sorted by ascending points. Here, the median 30 is at half of the 120 determined classifiers and has a probability value of 0.95.

The classification units/groups 9, 10, 11, 12 contained in an evaluation unit for defining the object information in the form of binary sex characteristics 31, 32—female or male— of fertilized and unincubated and incubated eggs 2 function as follows:

The functional principle will now be explained.

After the spectral preprocessing 5, 6, 7, 8, multiple classifiers of the series 13, 14, 15, 16 are calculated from each class 25, 26, 27, 28. The definition of the classifier series 13, 14, 15, 16 takes place according to an algorithm which, in a kind of tandem method, first selects spectral regions $R_S$ from the coordinate of the relative wavenumbers and then classifies the intensity values of the selected regions $R_S$ by means of discriminant analysis.

In a comparison with the training data for the class association, another selection of spectra classes and the classification of the intensity values occur in a repeated step. This cycle is repeated iteratively until an accuracy that can no longer be improved is reached, wherein the stopping criterion can be predefined.

The risk of overtraining, and therefore reaching high instabilities, grows as the number of spectral classes 25, 26, 27, 28 used for the classification increases. It is therefore desirable to use only a few (3 to maximally 20) spectral classes to create the classifier series 13, 14, 15, 16. However, because the sex-relevant information is distributed, albeit varyingly, across the entire spectral range, essential spectral information would actually remain unused if only one classifier were to be created. For this reason, it is expedient that multiple (10 to 20) classifiers in the series 13, 14, 15, 16 are calculated per group of data preprocessing 5, 6, 7, 8.

This has the advantage that, on the one hand, the accuracy of the classification is improved, solely based on the fact that the greatest possible amount of spectral information is incorporated, and that on the other hand the robustness, that is, the stability, is increased since multiple classifiers of the series 13, 14, 15, 16 support the assignment and individual erroneous assignments are compensated for.

The hardware units assigned to the classifications operate identically for all four groups 9, 10, 11, 12. Thus, instead of the four units controlled in parallel, it is also possible to use only one which creates the series 13, 14, 15, 16 of the classifiers serially in a predefined order. During the setting of the number of calculated classifiers $N_G$ in the series 13, 14, 15, 16 for each group 9, 10, 11, 12, the scale of the spectral data points $v_S$ and the doubled half-width of the spectral regions $w_S$ and also the number of selected spectral regions $R_S$ must be taken into account:

$$N_G = \frac{v_S}{2w_S \cdot R_S} \quad (I)$$

With the equation (I), it is ensured that each data point $v_S$ can be selected with equal probability.

In FIG. 10a and FIG. 10b, twenty classifiers per data preprocessing 25 are shown using the example of the raw spectra (intensity/wavenumber curves). For this purpose, FIG. 10 shows an enlarged section of the associated male intensity/wavenumber curves. The number of the spectral data points $v_S$ covers the entire spectral range between 500 $cm^{-1}$ and 2750 $cm^{-1}$. The number of the selected spectral regions $R_S$ in FIG. 10a is $R_S=8$, with $R_{S1}$, $R_{S2}$, $R_{S3}$, $R_{S4}$, $R_{S5}$, $R_{S6}$, $R_{S7}$, and $R_{S8}$.

According to equation (I), twenty classifiers $N_G$ can be calculated therefrom for the raw spectrum 25. With four data preprocessing methods 25, 26, 27, 28, this means a total of 80 classifiers generated (20 classifiers/group×4 groups).

According to the enlarged section in FIG. 10b, the data points $v_S$ can also be additionally weighted. For this purpose, a weighting chart 40 is shown in FIG. 10c, from which it is evident that the highest weighting value is assigned to the middle data point 41.

This can be performed both with the male spectrum and also with the female spectrum.

The evaluation 17 and the classification of the results assigned to the classifiers of the series 13, 14, 15, 16 are carried out in an evaluation unit and conducted until a classification result 18 (30) is produced.

Ultimately, a classification result 18 is outputted in the form of the median 30, which in the sex determination of chicken eggs represents the binary sex information 31, 32 (male or female) with the highest probability.

In general, the method according to the invention can be completed with the following detailed steps:

acquisition and recording of the spectra by means of at least one optical device having at least one spectrometer and/or additional detectors;

generating digitized signals in the form of data points, and storing the detected spectra in storage units of classification units of an evaluation unit;

spectral preprocessing, in that the stored spectra are individually evaluated in the individual storage units and the associated digitized evaluated signals are made available for further processing;

separating the preprocessed spectra as a training set and as a test set;

configuring the preprocessed spectra as a training set and a test set separate from the training set;

wherein according to the invention at least a calculation of the classifiers of the series of the integrated individual classification methods, with an incorporation of iterative methods and a validation in the classification groups;

classification of the evaluated spectra of the training set with all classifiers of the series;

placement of the spectra of the training set in a class of object information with an expression of a probability for the class association;

calculation of the median or performance of a cluster analysis to show the probability result of the training set object information associated with a class;

classification of the evaluated spectra of the test set with all classifiers of the series;

placement of the spectra of the test set in a class of object information with an expression of a probability for the class association; and calculation of the median or performance of a cluster analysis to show the probability result/classification result of the test set object information associated with a class.

are carried out.

It should also be noted that, by their very nature, the recorded spectra 4 are generally highly variable. This is based on the one hand on the inherent variability of biological systems and on the other hand on the sensitivity of Raman spectroscopic measurements. External interference of a systematic and random nature results in a high variability of the spectral characteristics and is thus superimposed on the characteristic-relevant information. Furthermore, in the method of Raman spectroscopy, fluorescent light is also present which likewise contains molecular information, but which is also superimposed on the normally much weaker Raman spectroscopic molecular information about the composition of the examined object 2.

On the basis of these preliminary remarks and FIG. 1, a further exemplary embodiment with more than two characteristics of object information will be explained. FIG. 1 shows in the schematic block diagram a method 1 according to the invention for classifying spectra 4 of an object 2 having complex information content, in particular optical molecular spectra 4, for assigning object information/characteristics 3 for a probabilistic definition, for example, of binary object information 31, 32 or of four pieces of object information 51, 52, 53, 54.

Tissue samples, for example, brain tumors, can also be used and applied as the objects 2 to be examined, and in place of the binary characteristic information 31, 32, four different characteristics 3 can for example also be selected and defined with 51, 52, 53, 54, for example
- characteristic 51: healthy tissue,
- characteristic 52: tumor tissue with tumor grade I and II according to the histological classification model of the World Health Organization (WHO),
- characteristic 53: tumor tissue with tumor grade III and IV according to the WHO, and
- characteristic 54: necrotic tissue.

The acquisition and recording of the backscatter radiation from the tissue sample occurs by means of at least one optical device as described, for example, in the publication DE 10 2014 010 150 A1. The recorded backscattering spectra 4 are digitized and stored in an evaluation unit. The data preprocessing occurs, for example, through three different methods 5, 6, 7; the data sets thereby obtained can, for example, respectively contain raw spectra, normalized spectra, and spectra with a non-linear baseline correction, wherein the stored spectra are individually evaluated in the individual storage units and the associated digitized evaluated signals are made available for further processing. The preprocessed spectra are configured as a training set, wherein according to the invention, a calculation is performed of the classifiers of the series of the integrated individual classification methods, with an incorporation of iterative methods and a validation in the classification units. Furthermore, the classification of the evaluated spectra of the test set takes place with all classifiers of the series, and the placement of the tissue spectra in a class of object information takes place according to the characteristics 51 through 54 with an expression of a probability for the class association. The classification is evaluated by the calculation of the mean or by means of a cluster analysis, and the probability result/classification result of the test set object information associated with a class is shown. This means that, for each recorded spectrum of a tissue sample, a score is calculated by means of multiple classification, which score lies in one of the 4 probability ranges according to set cut-offs, which ranges correspond to the histological findings of the following characteristics: 51—healthy/52—WHO I, II/53—WHO III, IV/54—necrosis.

Figure 1A:
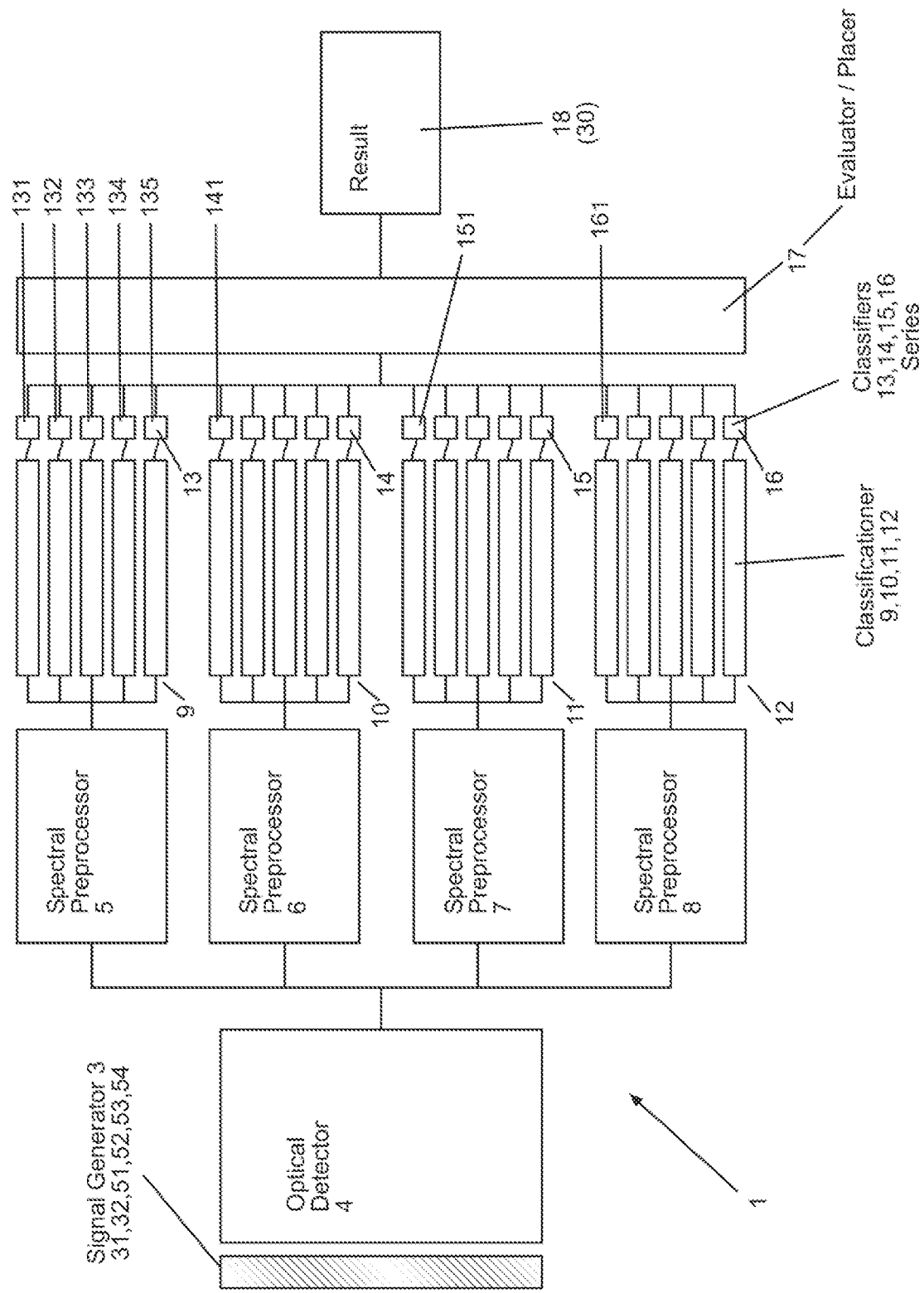
FIG. 1a shows apparatus for classifying spectra of objects having complex information content, preferably with objects in the form of chicken eggs for a determination of binary egg information—female or male—wherein the aforementioned method is implemented in the apparatus.

As shown in FIG. 1a, an apparatus for classifying spectra 4 of objects 2 having complex information content, preferably with objects in the form of chicken eggs 2 for a definition of binary egg information 31, 32—female or male—in which apparatus the aforementioned method is implemented and which is to a large extent embodied in accordance with the block diagram (box drawing) in FIG. 1, can comprise at least the following units:
- at least one optical detector 4 having at least one spectrometer and/or additional detectors for the acquisition and recording of the spectra 4;
- a signal generator 31, 32, 51, 52, 53, 54 for generating digitized signals in a form of data points by which the spectra are manifested 4;
- storage units for storing the recorded spectra 4 in the classification groups 9, 10, 11, 12 of an evaluator comprising the classification groups;
- a spectral preprocessor 5, 6, 7, 8 in which the stored spectra 4 are individually evaluated in the individual storage units and the associated digitized evaluated signals are made available for further processing;
- training sets 19 for configuring and using the preprocessed spectra 4; 25, 26, 27, 28;
- at least one classiticationer for the classification groups 9, 10, 11, 12 for calculating the classifiers of the series 13, 14, 15, 16 for the integrated individual conventional classification methods 25, 26, 27, 28, with an incorporation of iterative methods and a validation in the classification groups;
- test sets 29 for classifying the evaluated spectra 4 with all classifiers of the series 13, 14, 15, 16;
- a placer for placing the preprocessed spectra 4 in a, for example, binary class—male 32 or female 31—of object (egg) information with an expression of a probability for the class association;
- an evaluator to calculate the classification result 18 in the form of the median 30 or after performing a cluster analysis to show the probability result of the object (egg) information 31, 32 associated, for example, with one of the binary classes-female or male.

A similar apparatus can be constructed for the multiple classification method with the four characteristics 51, 52, 53, 54 or with additional predefined characteristics.

LIST OF REFERENCE NUMERALS

1 Method/Apparatus in a box drawing
2 Object/egg
3 Object information/characteristics
4 Recorded spectra/Detector
5, 6, 7, 8 Preprocessing/Spectral Preprocessors
9, 10, 11, 12 Classification/Classiicationer
13, 14, 15, 15, 16 Series of classifiers
131, 132, 133, 134, 135, 136 Classifier
17 Evaluation/Evaluator
18 Classification result
19 Training set
20 Molecular composition
21 Fluorescence intensity
22 Fluorescence profile
23 Variation of physical parameters
24 Classified test set
25, 26, 27, 28 Preprocessed spectra
29 Test set with preferably 30% of the spectra selected
30 Median
31 Female object information/characteristic/Signal Generator
32 Male object information/characteristic/Signal Generator
33 Unshaded front face, assigned to the female sex
34 Bar for the female sex 35 Bar for the male sex
36 Shaded front face, assigned to the male sex
37 Classification result image
38, 39 Bar graph
40 Weighting chart
41 Middle data point in the region of a spectrum curve
42 Set cut-off
43 First histogram of the cluster analysis
44 Second histogram of the cluster analysis
45=① comparison node
46=② comparison node
47=⑤ comparison node
48=③ comparison node
49=④ comparison node
50 Classifier according to the prior art
51, 52, 53, 54 Characteristic/Signal Generator

The invention claimed is:

1. A method for classifying spectra of eggs, comprising:
recording spectral data related to an egg;
preprocessing the spectral data with at least two different spectral preprocessing methods performed in parallel to produce preprocessed outputs;
classifying each of the preprocessed outputs with a respective classifier to produce classification outputs;
calculating a probability related to a class association for each of the classification outputs; and
calculating a final classification result for the egg based on the classification outputs and the probabilities.

2. The method according to claim 1, wherein a number of classifiers ($N_G$) is calculated according to the following equation:

$$N_G = \frac{v_S}{2w_S \cdot R_S}$$

wherein $v_S$ is a number of spectral data points in the spectral data, $w_S$ is a doubled half-width of a spectral region in the spectral data, and $R_S$ is a number of spectral regions analyzed in the spectral data; and
wherein there is an equal probability of a respective data point in the spectral data being sampled.

3. The method according to claim 2, wherein data points belonging to the number of the spectral data points ($v_S$) are weighted.

4. The method according to claim 1, wherein: at least one of the spectral preprocessing methods is structured such that respectively defined characteristics become prominent and other defined characteristics are suppressed.

5. The method according to claim 4, further comprising: adding at least one spectral preprocessing method with equivalently defined and equally weighted characteristics to at least one of the spectral preprocessing methods with differently defined characteristics for evaluation.

6. The method according to claim 1, wherein:
prepossessed spectra are designed as a training set and at least one classifier is defined and validated by the training set.

7. The method according to claim 1, further comprising: using at least one method of unsupervised classification or supervised classification to select spectral regions $R_S$ or individual wavelength ranges in the spectral data for subsequent analysis.

8. The method according to claim 1, wherein at least one classifier utilizes a neural network or a linear wavelet transform.

9. The method according to claim 1, further comprising: using a neural network method or a linear wavelet transform method as a method for classification in classification groups.

10. The method according to claim 1, wherein: preprocessed spectra are classified using optical molecular spectroscopy.

11. The method according to claim 1, wherein:
preprocessed spectra are classified using optical molecular spectroscopy selected from absorption, emission, scattering, UV/vis, NIR, IR absorption, fluorescence, and Raman.

12. The method according to claim 1, wherein at least one of the spectral preprocessing methods comprises any one or more of the following: raw spectra, baseline corrections, normalizations, derivatives, covariance, or Raman spectra.

13. The method according to claim 1, wherein a calculation of a median or performance of a cluster analysis is carried out for evaluation of the classifiers for a classification result.

14. The method according to claim 1, further comprising:
acquiring the spectral data via at least one optical device having at least one spectrometer;
storing the spectral data in at least two storage units;
performing the preprocessing of the spectral data by independently preprocessing respective spectral data stored in each storage unit;
separating and configuring the preprocessed spectra data as a training set and as a test set;
calculating the classification outputs using an iterative method and validating the classification outputs;
classifying the preprocessed spectral data of the training set using the classifiers;
placing the spectral data of the training set in a class of object information with an expression of probability for a class association;
calculating a classification result by calculating a median or by performing a cluster analysis to show a probability result for the training set;
classifying the preprocessed spectral data of the test set using the classifiers;
placing the spectral data of the test set in a class of object information with an expression of probability for a class association;
calculating a classification result by calculating a median or by performing a cluster analysis to show a probability result for the test set.

15. The method according to claim 1, wherein the egg is a bird egg the final classification result is related to a sex of the bird egg.

16. The method according to claim 1, wherein the egg is a chicken egg and the final classification result is related to a sex of the bird egg.

17. The method of claim 1, wherein:
each classifier analyzes different spectral data; and
the classification outputs are aggregated and a highest probability associated with the classification outputs is utilized in determining the final classification result.

18. An apparatus for classifying spectra of objects having complex information content, in which the method according to claim 1 is implemented, comprising at least the following:
at least one optical detector having at least one spectrometer or additional detectors for the acquisition and recording of spectral data;
storage units for storing the spectral data;

spectral preprocessors configured to independently preprocess respective spectral data stored in each storage unit;
at least one classificationer for calculating a classifier based on the spectral data, with an incorporation of iterative methods and validating the classifier;
a placer for placing the preprocessed spectral data in at least class of object information with an expression of a probability for a class association;
an evaluator to calculate a classification result, in the form of the median or performing a cluster analysis for determining the probability result.

* * * * *